(12) United States Patent
Jacobsen et al.

(10) Patent No.: US 6,844,448 B2
(45) Date of Patent: Jan. 18, 2005

(54) MAIN-GROUP METAL-BASED ASYMMETRIC CATALYSTS AND APPLICATIONS THEREOF

(75) Inventors: Eric N. Jacobsen, Boston, MA (US); Matthew S. Sigman, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/325,592

(22) Filed: Dec. 20, 2002

(65) Prior Publication Data

US 2003/0187249 A1 Oct. 2, 2003

Related U.S. Application Data

(62) Division of application No. 09/071,842, filed on May 1, 1998, now Pat. No. 6,521,561.

(51) Int. Cl.[7] ..................... C07D 207/40; C07C 253/00; C07C 229/00

(52) U.S. Cl. .................. 548/546; 558/335; 560/37; 560/41

(58) Field of Search .................. 548/546; 558/335; 560/37, 41

(56) References Cited

U.S. PATENT DOCUMENTS

| | | | |
|---|---|---|---|
| 4,497,964 A | 2/1985 | Ojima et al. | |
| 4,751,068 A | 6/1988 | Bickar et al. | ............... 423/437 |
| 5,177,109 A | 1/1993 | Pellicciari et al. | |
| 5,332,826 A | 7/1994 | Buckland | |
| 5,350,851 A | 9/1994 | Bailey et al. | |
| 5,523,455 A | 6/1996 | Labeeuw et al. | |
| 5,612,484 A | 3/1997 | Askin et al. | |
| 5,750,566 A | 5/1998 | Monn et al. | |
| 5,981,783 A | * 11/1999 | Polt | ........................... 556/138 |
| 6,130,340 A | * 10/2000 | Jacobsen et al. | ............ 549/273 |

FOREIGN PATENT DOCUMENTS

| | | |
|---|---|---|
| EP | 0 641 762 A1 | 3/1995 |
| JP | 05286919 A | 11/1993 |
| WO | WO 91/17141 | 11/1991 |
| WO | WO 99/51546 | 10/1999 |

OTHER PUBLICATIONS

U.S. patent application Ser. No. 60/043,855, Polt, filed Apr. 1997.*
Vincens et al, Stereoselective Olgomerization of Methyloxirane with a Chiral Aluminum Complex of a Schiff's Base as Initiator Makromol. Chem., Rapid Commun., vol. 10, pp. 623–628 (1989).*
Hawley's Condensed Chemical Dictionary, 13th ed. © 1997 by Van Nostrand Reinhold. pp. 157, 535, 996.*
Taden et al, "Aluminum Complexes of Sterically Hindered Tetradentate Schiff Bases: synthesis, structure, and reactivity toward e–caprolactone" Journal of Organometallic Chemistry, vol. 540, pp. 189–192 (1997).*
Mann et al, "Configuration Energies of the Main Group Elements" J. Am. Chem. Soc. vol. 122, pp. 2780–2783 (2000).*
Petrie, S., "Chemistry in Stringland: One–Dimensional Complexes of Main–Group Metal Ions with the Ligands NC2nX (X=N, CH n=0,1,2,3)" J. Phys. Chem. vol. 107, pp. 10441–10449 (2003).*
Atwood et al.; "A New Class of Aluminum Cations Based Upon Tetradentate (N2 O2 ) Chelating Ligands" Inorg. Chem. 35: 63–70, (1996).
Bousquet, C. et al., "Auxiliaires Cétoniques Chiraux dans la Synthèse Asymétrique des α–Aminoacides Selon Strecker," *Bull Soc. Chim. Fr.* pp. 513–520, 130, 1993.
Chataigner, I., et al. "Enantioselective Synthesis of α–Methylene–γ–Lactams. Nucleophilic Addition of a Chirally Modified β–Functionalized Allylboronate Reagent to Imines," *SYNLETT*, pp. 275–276, Mar. 1998.
Enders, D. et al., "Asymmetric Synthesis of Amines by Nucleophilic 1,2–Addition of Organometallic Reagents to the CN–Double Bond," *Tetrahedron: Asymmetry*, vol. 8, No. 12, pp. 1895–1946, 1997.
Fadel, A., et al., "A Straightforward Synthesis of Both Enantiomers of Allo–Norcoronamic Acids and Allo–Coronamic Acids, by Asymmetric Strecker Reaction from Alkylcyclopropanone Acetals," *Tetrahedron: Asymmetry* 9 pp. 305–320, 1998.
Ferraris, D., et al, "Catalytic, Enantioselective Alkylation of α–Imino Esters Using Late Transition Metal Phosphine Complexes as Catalysts," *J. Am. Chem. Soc.*, 120, pp. 4548–4549, 1998.
Groves and Myers, "Catalytic Asymmetric Epoxidations with Chiral Iron Porphyrins", J.A.C.S., 105(18):5791–5796, (1983).
Harada, K., et al., "Sterically Controlled Syntheses of Optically Active Organic Compounds. XIX. Asymmetric Syntheses of Amino Acids by the Strecker Reaction," *Bulletin of the Chemical Society of Japan*, vol. 46, pp. 1865–1868, 1973.
Huber, R., et al., "Asymmetric Synthesis of N–Hydroxy–α–Aminophosphonic and α–Aminophosphonic Acids," *Helvetica Chemica Acta*, vol. 70, pp. 1461–1476, 1987.

(List continued on next page.)

*Primary Examiner*—James O. Wilson
*Assistant Examiner*—Zachary C. Tucker
(74) *Attorney, Agent, or Firm*—Dana M. Gordon; Foley Hoag LLP

(57) ABSTRACT

The present invention relates to a method and catalysts for the stereoselective addition of a nucleophile to a reactive π-bond of a substrate. The chiral, non-racemic catalysts of the present invention constitute the first examples of catalysts for nucleophilic additions that comprise a main-group metal and a tri- or tetra-dentate ligand.

64 Claims, No Drawings

OTHER PUBLICATIONS

Iyer et al.;"Asymmetric Catalysis of the Strecker Amino Acid Synthesis by a Cyclic Dipeptide", J. Am. Chem. Soc. 118: 4910–4911, (1996).

Kunz, H., et al., "Stereoselective Synthesis of L–Amino Acids via Strecker and Ugi Reaktions on Carbohydrate Templates," *Synthesis*, pp. 1039–1042, Nov. 1991.

Kunz, H., et al., "Reversal of Asymmetric Induction in Stereoselective Strecker Synthesis on Galactosyl Amine as the Chiral Matrix," *Tetrahedron Letters*, vol. 29, No. 35, pp. 4397–4400, 1988.

Kuwano, R., et al., "Catalytic Asymmetric Synthesis of β–Hydroxy–α–amino Acids: Highly Enantioselective Hydrogenation of β–Oxy–α–acetamidoacrylates," *J. Org. Chem.*, 63, pp. 3499–3503, 1998.

Richards, C.J., et al., "Nucleophilic Addition to Vinylketenimine Complexes. The Asymmetric Synthesis of Carbon Quaternary Centres," *Tetrahedron: Asymmetry*, vol. 3, No. 1, pp. 143–160, 1992.

Shono, T., et al., "New Synthesis of β–Amino Acids by Nucleophilic Addition of Enolate Anions to N–Methoxycarbonylimines Generated from α–Methoxy Carbamates," *Tetrahedron Letters*, vol. 29, No. 2, pp. 231–234, 1988.

Sigman, M.S., et al., "Enantioselective Addition of Hydrogen Cyanide to Imines Catalyzed by a Chiral (Salen) Al(III) Complex," *J. Am. Chem. Soc.* 120, pp. 5315–5316, 1998.

Sigman, M.S., et al., "Schiff Base Catalysts for the Asymmetric Strecker Reaction Identified and Optimized from Parallel Synthetic Libraries," *J. Am. Chem. Soc.*, 120, pp. 4901–4902, 1998.

Stout, D.M., et al., "Asymmetric Strecker Synthesis: Isolation of Pure Enantiomers and Mechanistic Implications," *J. Org. Chem.*, 48, pp. 5369–5373, 1983.

Weinges, K., et al., "Über Die Asymmetrische Strecker–Synthese mit (S)–(–)–1–Phenylethylamin als Chiralem Hilfsreagens," *Chem. Ber.* 110, pp. 2098–2105, 1977.

Weinges, K., et al., "Die Asymmetrische Strecker–Synthese von Aliphatischen α–Methyl–α–Aminosäuren," *Chem. Ber.* 106, pp. 2291–2297, 1973.

Yamamoto, Y., et al., "Transition Metal Catalyzed Addition of Certain Nucleophiles to Imines," *J. Am. Chem. Soc.* 116, pp. 3161–3162, 1994.

\* cited by examiner

MAIN-GROUP METAL-BASED ASYMMETRIC CATALYSTS AND APPLICATIONS THEREOF

This application is a divisional of U.S. patent application Ser. No. 09/071,842, filed May 1, 1988, now U.S. Pat. No. 6,521,561.

GOVERNMENT FUNDING

Work described herein was supported in part with funding from the National Institutes of Health. The United States Government has certain rights in this invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include fewer side effects and greater potency of enantiomerically pure compounds.

Traditional methods of organic synthesis have often been optimized for the production of racemic materials. The production of enantiomerically pure material has historically been achieved in one of two ways: the use of enantiomerically pure starting materials derived from natural sources (the so-called "chiral pool"); or the resolution of racemic mixtures by classical techniques. Each of these methods has serious drawbacks, however. The chiral pool is limited to compounds found in nature, so only certain structures and configurations are readily available. Resolution of racemates often requires the use of resolving agents; this process may be inconvenient and is certain to be time-consuming. Furthermore, resolution often means that the undesired enantiomer is discarded, thereby wasting half of the material.

SUMMARY OF THE INVENTION

In one aspect of the present invention, there is provided a process for enantioselective chemical synthesis which generally comprises the addition of a nucleophile to a π-bond in the presence of a non-racemic chiral catalyst to produce a enantiomerically enriched product. The π-bond containing substrate comprises a carbon-carbon or carbon-heteroatom π-bond, the nucleophile is typically the conjugate base of a weak acid, and the chiral catalyst comprises an asymmetric tetradentate or tridentate ligand complexed with a main-group metal ion. In the instance of the tetradentate ligand, the catalyst complex has a rectangular planar or rectangular pyramidal geometry. The tridentate ligand-metal complex assumes a planar or trigonal pyramidal geometry. In a preferred embodiment, the ligand has at least one Schiff base nitrogen complexed with the metal at the core of the catalyst. In another preferred embodiment, the ligand provides at least one stereogenic center within two bonds of a ligand atom which coordinates the metal.

In general, the metal atom is a main-group metal from Groups 1, 2, 12, 13, or 14 and may be in its highest state of oxidation. In preferred embodiments, the metal atom is selected from the group comprising Li, Be, Na, Mg, K, Ca, B, Al, Ga, In, Zn, Cd, Hg, Si, Ge, and Sn. In highly preferred embodiments, the metal is Al.

Exemplary substrates for the subject asymmetric nucleophilic addition reaction include aldehydes, enals, ketones, enones, enoates, α,β-unsaturated imides, imines, oximes, and hydrazones.

In preferred embodiments, the subject transformation can be represented by the conversion of 1 to 2, wherein the asterisk in 2 indicates an asymmetric center.

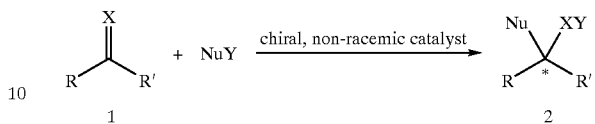

wherein
R, R', and R'' represent, independently for each occurrence, hydrogen, alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or $-(CH_2)_m-R_{80}$;

X is selected from the group comprising $CR_2$, O, S, Se, and NR'';

Y is selected, independently for each occurrence, from the set comprising H, Li, Na, K, Mg, Ca, B, Al, Cu, Ag, Ti, Zr, $SiR_3$ and $SnR_3$; and Nu is selected from the set comprising conjugate bases of weak Bronsted acids—e.g. cyanide, azide, isocyanate, thiocyanate, alkoxide, thioalkoxide, carboxylate, thiocarboxylate—and carbanions;

$R_{80}$ represents an unsubstituted or substituted aryl, a cycloalkyl, a cycloalkenyl, a heterocycle, or a polycycle; and m is an integer in the range 0 to 8 inclusive.

In a preferred embodiment, the method includes combining a substrate that comprises a reactive π-bond, a nucleophile, and a non-racemic chiral catalyst as described herein, and maintaining the combination under conditions appropriate for the chiral catalyst to catalyze a stereoselective addition of the nucleophile to a reactive π-bond of the substrate.

In preferred embodiments, the chiral catalyst which is employed in the subject reaction is represented by the general formula:

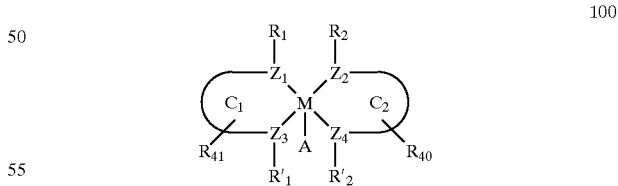

in which
$Z_1$, $Z_2$, $Z_3$ and $Z_4$ each represent a Lewis base;
the $C_1$ moiety, taken with $Z_1$, $Z_3$ and M, and the $C_2$ moiety, taken with $Z_2$, $Z_4$ and M, each, independently, form a heterocycle;
$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is take together with at least one of $R_2$, $R'_2$ and $R_{40}$ to form a bridging substituent so as to provide $Z_1$, $Z_2$, $Z_3$ and $Z_4$ as a tetradentate;

M represents the main-group metal ion; and

A represents a counterion or a nucleophile, wherein each $R_1$, $R_2$, $R'_1$, $R'_2$ $R_{40}$ and $R_{41}$ are selected to provide at least one stereogenic in the tetradentate ligand.

In exemplary embodiments, $R_1$, $R_2$, $R'_1$ and $R'_2$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$;

each $R_{40}$ and $R_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$;

$R_8$ represents an aryl, a cycloalkyl, a cycloalkenyl, a heterocycle or a polycycle;

$Z_1$, $Z_2$, $Z_3$ and $Z_4$ are independently selected from the group consisting of nitrogen, oxygen, phosphorus, arsenic, and sulfur; and m is zero or an integer in the range of 1 to 8.

For example, the catalyst can be represented by the general formula:

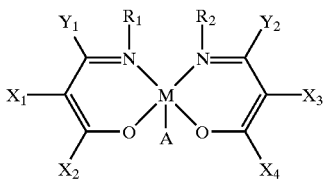

in which the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$, or any two or more of the substituents taken together form a carbocyle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;

$R_8$ represents an aryl, a cycloalkyl, a cycloalkenyl, a heterocycle, or a polycycle;

m is zero or an integer in the range of 1 to 8;

M represents the main-group metal; and

A represents a counterion or a nucleophile, wherein each of of the substituents $R_1$, $R_2$, $Y_1$, $Y_2$, $X_1$, $X_2$, $X_3$ and $X_4$, are selected such that the catalyst is asymmetric.

For example, a preferred class of catalysts are represented by the general formula:

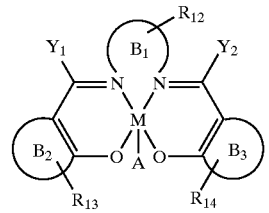

in which the $B_1$ moiety represents a diimine bridging substituent represented by —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sufonyl, a selenium, a carbonyl, or an ester;

each of $B_2$ and $B_3$ independently represent rings selected from a group consisting of cycloalkyls, cycloakenyls, aryls, and heterocyclic rings, which rings comprising from 4 to 8 atoms in a ring structure;

$Y_1$ and $Y_2$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$, $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$, wherein $R_{12}$ can occur on one or more positions of —$R_{15}$—$R_{16}$—$R_{17}$—, or any two or more of the $R_{12}$, $R_{13}$, $R_{14}$, $Y_1$ and $Y_2$ taken together form a bridging substituent;

$R_8$ represents an aryl, a cycloalkyl, a cycloalkenyl, a heterocycle, or a polycycle;

m is zero or an integer in the range of 1 to 8;

M represents a main-group metal; and

A represents a counterion or a nucleophile, wherein $R_{12}$, $R_{13}$, $R_{14}$, $Y_1$ and $Y_2$ are selected such that the catalyst is asymmetric.

In yet further preferred embodiments, the catalyst is a metallosalenate catalyst represented by the general formula:

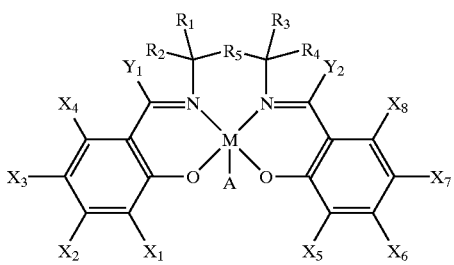

in which
each of the substituents $R_1, R_2, R_3, R_4, R_5, Y_1, Y_2, X_1, X_2, X_3, X_4, X_5, X_6, X_7,$ and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_8$;

or any two or more of the substituents taken together form a carbocycle or heterocycle having from 4 to 10 atoms in the ring structure;

$R_8$ represents an aryl, a cycloalkyl, a cycloalkenyl, a heterocycle or a polycycle; m is zero or an integer in the range of 1 to 8;

M represents a main-group metal; and

A represents a counterion or a nucleophile;

wherein if $R_5$ is absent, at least one of $R_1$ and $R_2$ is taken together with at least one of $R_3$ and $R_4$ to form a bridging substituent, and each of of the substituents of 106 are selected such that the salenate is asymmetric.

Alternatively, the catalyst can have a tridentate ligand, such as the ligand represented by the general formula:

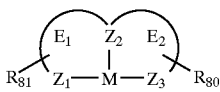

in which
$Z_1, Z_2,$ and $Z_3$ each represent a Lewis base;

the $E_1$ moiety, taken with $Z_1, Z_2$ and M, and the $E_2$ moiety, taken with $Z_2, Z_3$ and M, each, independently, form a heterocycle;

$R_{80}$ and $R_{81}$ each independently are absent, hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or $-(CH_2)_m-R_8$, or any two or more of the $R_{80}$ and $R_{81}$ substituents taken together form a bridging substituent;

$R_8$ represents an aryl, a cycloalkyl, a cycloalkenyl, a heterocycle or a polycycle;

m is zero or an integer in the range of 1 to 8;

M represents a main-group metal; and

A represents a counteranion or a nucleophile; and wherein the tridentate ligand is asymmetric.

DETAILED DESCRIPTION OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include fewer side effects and greater potency of enantiomerically pure compounds. As described herein, the present invention makes available methods and reagents for enantioselective synthesis involving nucleophilic addition reactions. The primary constituents of the method, set out in more detail below, are a chiral, non-racemic metal catalyst of particular tetradentate or tridentate geometry; a chiral or prochiral carbon-carbon or carbon-heteroatom π-bond, and a nucleophile—typically a weak acid or its conjugate base; the substrate containing the reactive π-bond, and the nucleophile are chosen so that the outcome of the reaction is influenced by the presence of the aforementioned chiral, non-racemic catalyst.

I. Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like may, under approriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base as defined above.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term, "chelating agent" refers to an organic molecule having unshared electron pairs available for donation to a metal ion. The metal ion is in this way coordinated by the chelating agent.

The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent.

The term "catalyst" refers to a substance the presence of which increases the rate of a chemical reaction, while not being consumed or undergoing a permanent chemical change itself.

The terms, "bidentate catalyst", "tridentate catalyst", and "tetradentate catalyst" refer to catalysts having, respectively, two, three, and four contact points with the substrate of the catalyst.

The term "coordination" refers to an interaction in which an electron pair donor coordinatively bonds (is "coordinated") to one metal ion.

The term "coordinate bond" refers to an interaction between an electron pair donor and a coordination site on a metal ion leading to an attractive force between the electron pair donor and the metal ion.

The term "coordination site" refers to a point on a metal ion that can accept an electron pair donated, for example, by a chelating agent.

The term "free coordination site" refers to a coordination site on a metal ion that is occupied by a water molecule or other species that is weakly donating relative to a polyamino acid tag, such as a histidine tag.

The term "coordination number" refers to the number of coordination sites on a metal ion that are available for accepting an electron pair.

The term "complex" as used herein and in the claims means a coordination compound formed by the union of one or more electron-rich and electron-poor molecules or atoms capable of independent existence with one or more electronically poor molecules or atoms, each of which is also capable of independent existence.

The term "ring expansion" refers to a process whereby the number of atoms in a ring of a cyclic compound is increased. An illustrative example of ring expansion is the reaction of epoxides with carbon dioxide to yield cyclic carbonates.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, $2^{nd}$ ed.; Wiley: New York, 1991).

The term "meso compound" is recognized in the art and means a chemical compound which has at least two chiral centers but is achiral due to the presence of an internal plane or point of symmetry.

The term "chiral" refers to molecules which have the property of non-superimposability of their mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoisomerically-enriched" product (e.g., enantiomerically-enriched or diastereomerically-enriched) when the yield of a particular stereoisomer of the product is greater by a statistically significant amount relative to the yield of that stereoisomer resulting from the same reaction run in the absence of a chiral catalyst. For example, a reaction which routinely produces a racemic mixture will, when catalyzed by one of the subject chiral catalysts, yield an e.e. for a particular enantiomer of the product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant majority of a certain regioisomer.

The term "reaction product" means a compound which results from the reaction of the two substrate molecules. In general, the term "reaction product" will be used herein to refer to a stable, isolable compound, and not to unstable intermediates or transition states.

The term "complex" as used herein and in the claims means a coordination compound formed by the union of one or more electronically rich molecules or atoms capable of independent existence with one or more electronically poor molecules or atoms, each of which is also capable of independent existence.

The term "substrate" is intended to mean a chemical compound which can react under the subject conditions to yield a product having at least one stereogenic center.

The term "catalytic amount" is recognized in the art and means a substoichiometric amount of the catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess $A$ (ee) = (% enantiomer $A$) − (% enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a reactant or reactants (which may be achiral, racemic, non-racemic or enantiomerically pure) to a product enriched in one diastereomer. If the chiral reactant is racemic, in the presence of a chiral, non-racemic reagent or catalyst, one reactant enantiomer may react more slowly than the other. This effect is termed a kinetic resolution, wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective cycloaddition reaction of an unsymmetrical 1,3,5-triene substrate would preferentially occur at one of the two 1,3-dienes contained therein.

The term "non-racemic" means a preparation having greater than 50% of a desired stereoisomer, more preferably at least 75%. "Substantially non-racemic" refers to preparations which have greater than 90% ee for a desired stereoisomer, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, an alkoxyl, a silyloxy, a carbonyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (inlcuding phosphonates and phosphines), sulfonyls (inlcuding sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, an "amine" can be represented by the general formula:

wherein $R_8$ and $R_9$ each independently represent a hydrogen, an alkyl, an alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

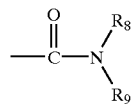

wherein $R_8$ and $R_9$ are as defined above.

The term "alkylimine" refers to an alkyl group having a substituted or unsubstituted imine attached thereto. An "imine" can be represented by the general formula:

wherein $R_8$ is as described above.

The term "thioalkyl" refers to an alkyl group, as defined above, having a sulfhydryl or thioether group attached thereto. In preferred embodiments, the "thioether" moiety is represented by one of —S-alkyl, —S-alkenyl, —S-alkynyl, and —S—$(CH_2)_m$—$R_7$, wherein m and $R_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

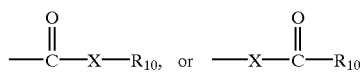

wherein X is absent or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, the formula represents an "ester". Where X is a sulfur, the formula represents a "thioester." Where X is absent, and $R_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O-alkyl, —O-alkenyl, —O-alkynyl, —O—$(CH_2)_m$—$R_7$, where m and $R_7$ are described above.

Thus, the term "phosphorylalkyl" as used herein means an alkyl group, as defined above, having a substituted or unsubstituted phosphoryl group attached thereto. A "phosphoryl" can in general be represented by the formula:

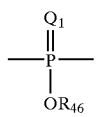

wherein $Q_1$ represented S or O, and $R_{46}$ represents hydrogen, a lower alkyl or an aryl. When used to substitute an alkyl, the phosphoryl group of the phosphorylalkyl can be represented by the general formula:

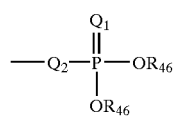

wherein $Q_1$ represented S or O, and each $R_{46}$ indepedently represents hydrogen, a lower alkyl or an aryl, $Q_2$ represents O, S or N.

The term "metalloalkyl" refers to an alkyl group, as defined above, having a substituted or unsubstituted orga-nometallic group attached thereto. A "silyl alkyl" is an alkyl having a substituted silicon attached thereto. In a preferred embodiment, the "silyl" moiety which may be substituted on the alkyl can be represented by the general formula:

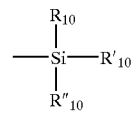

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, a "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

The term "sulfonyl" as used herein means a $S(O)_2$ moiety bonded to two carbon atoms. Thus, in a preferred embodiment, a sulfonate has the following structure:

wherein the single bonds are between carbon and sulfur.

The term "sulfonate" as used herein means a sulfonyl group, as defined above, attached to a hydroxyl, alkyloxy or aryloxy group. Thus, in a preferred embodiment, a sulfonate has the structure:

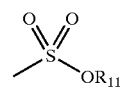

in which $R_{11}$ is absent, hydrogen, alkyl, or aryl.

The term "sulfate", as used herein, means a sulfonyl group, as defined above, attached to two hydroxy or alkoxy groups. Thus, in a preferred embodiment, a sulfate has the structure:

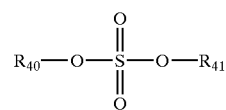

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R_{15}$—$R_{16}$—$R_{17}$—, wherein $R_{15}$ and $R_{17}$ each independently are absent or represent an alkyl, an alkenyl, or an alkynyl, preferably $C_1$ to $C_{10}$, and $R_{16}$ is absent or represents an amine, an imine, an amide, a phosphoryl a carbonyl, a silyl, an oxygen, a sulfonyl, a sulfer, a selenium, or an ester. Exemplary bridging substituents are given by the "picnic basket" forms of, for instance, the porphoryn catalysts described below.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "amino acid" is intended to embrace all compounds, whether natural or synthetic, which include both an amino functionality and an acid functionality, including amino acid analogs and derivatives. Also included in the term "amino acid" are amino acid mimetics such as β-cyanoalanine, norleucine, 3-phosphoserine, homoserine, dihydroxyphenylalanine, 5-hydroxytryptophan, and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

II. Catalyzed Reactions

In one aspect of the present invention there is provided a process for stereoselectively producing compounds with at least one stereogenic center. An advantage of this invention is that enantiomerically enriched products can be synthesized from achiral or racemic reactants. Another advantage is that yield loses associated with the production of an undesired enantiomer can be substantially reduced.

In general, the invention features a stereoselective nucleophilic addition process which comprises combining a substrate comprising a reactive π-bond, a nucleophile, and at least a catalytic amount of a non-racemic, chiral catalyst of particular characteristics (as described below). The combination is maintained under conditions appropriate for the chiral catalyst to catalyze stereoselective addition of the nucleophile to a reactive π-bond of the substrate. This reaction can be applied to enatioselective processes as well as diastereoselective processes. It may also be adapted for regioselective reactions. Examples of enantioselective reactions, kinetic resolution, and regioselective reactions which may be catalyzed according to the present invention follow.

In an exemplary embodiment, cyanide ion adds to the carbon of an imine functional group in the presence of a subject chiral, non-racemic catalyst yielding a non-racemic α-amino nitrile product. This embodiment is an example of a subject enantioselective nucleophilic addition reaction. The product of this reaction can be transformed in a single step to non-racemic N-methyl phenylglycine—a non-natural α-amino acid.

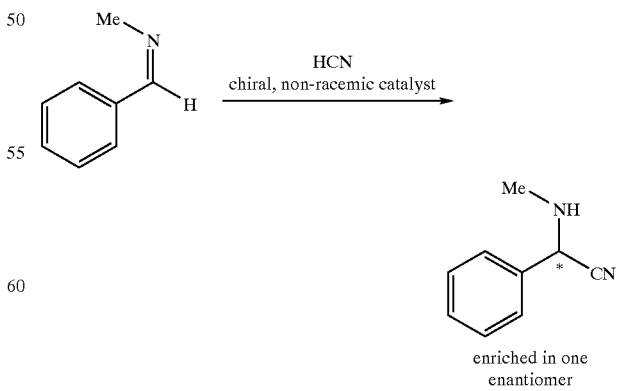

enriched in one enantiomer

In another aspect of the invention, the nucleophilic addition reaction occurs in a diastereoselective manner in the presence of a chiral, non-racemic catalyst. An illustrative example of a diastereoselective reaction of the present invention is shown below.

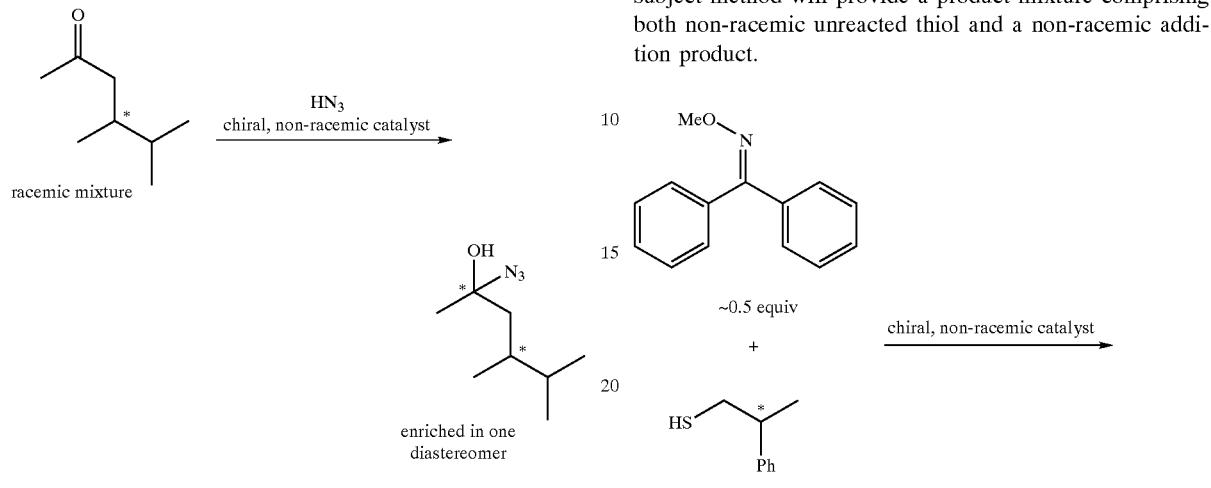

In another illustrative embodiment, the present invention provides a method for the kinetic resolution of a racemic mixture of an imine containing an α-stereocenter. In the subject catalyst-mediated kinetic resolution process involving a racemic imine substrate, one enantiomer of the imine can be recovered as unreacted substrate while the other is transformed to the desired product. This aspect of the invention provides methods of synthesizing functionalized non-racemic products from racemic starting materials. This embodiment is a diastereoselective process as well.

A second type of kinetic resolution possible with the subject method involves the resolution of a racemic nucleo-phile. The exemplary embodiment shown below centers on the resolution of a racemic mixture of thiols in catalyzed reaction with O-methyl benzophenone oxime. Use of approximately 0.5 equivalents of the oxime ether in the subject method will provide a product mixture comprising both non-racemic unreacted thiol and a non-racemic addition product.

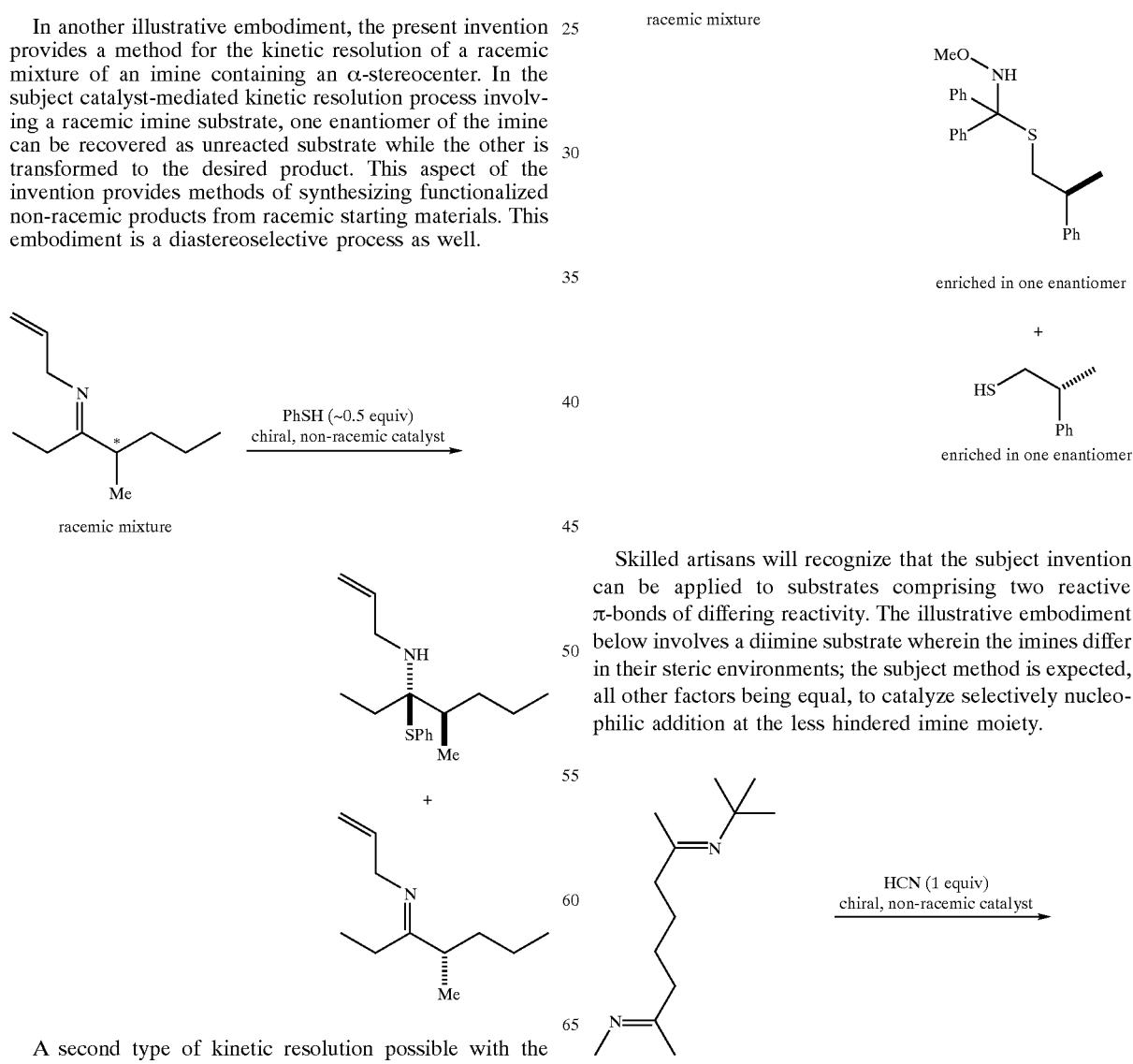

Skilled artisans will recognize that the subject invention can be applied to substrates comprising two reactive π-bonds of differing reactivity. The illustrative embodiment below involves a diimine substrate wherein the imines differ in their steric environments; the subject method is expected, all other factors being equal, to catalyze selectively nucleophilic addition at the less hindered imine moiety.

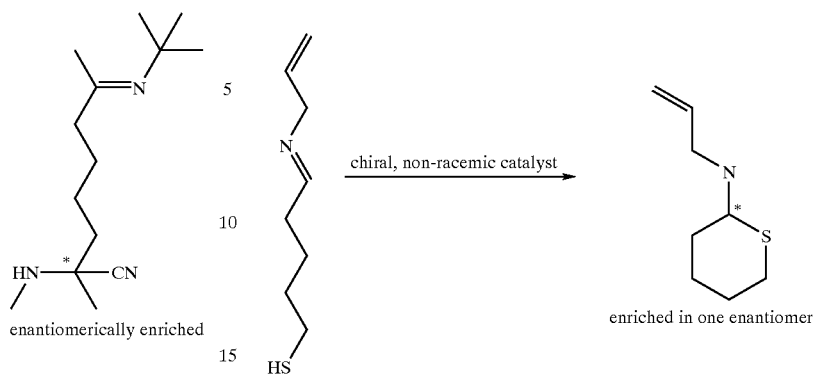

Additionally, skilled artisans will recognize that the subject invention can be applied to substrates comprising different classes of reactive π-bonds. The illustrative embodiment below involves a substrate that comprises both an imine and a hydrazone. The subject method is expected, all other factors being equal, to catalyze nucleophilic addition at the imine moiety.

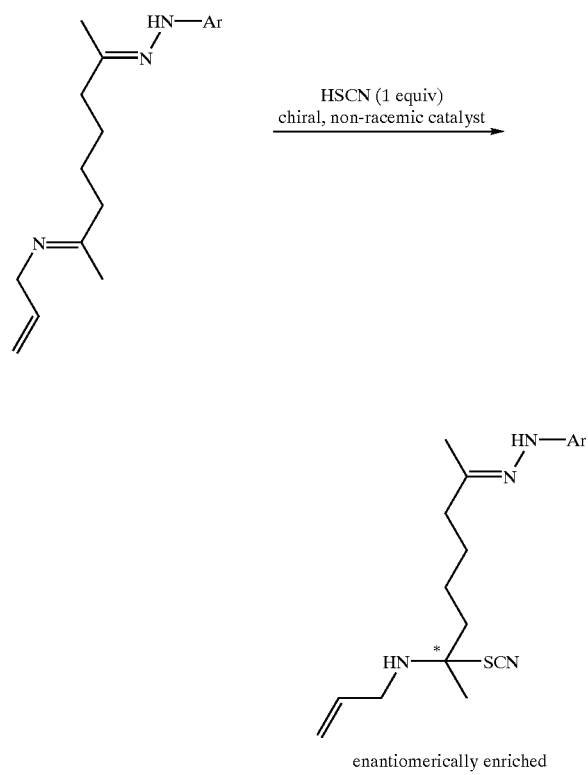

The subject method and catalysts may also be exploited in an intramolecular sense. In the illustrative embodiment that follows, the chiral, non-racemic catalyst catalyzes the intramolecular enantioselective addition of a thiol to an N-allyl imine.

The processes of this invention can provide optically active products with very high stereoselectivity (e.g., enantioselectivity or diasteroselectivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions, molar ratios for desired/undesired regioisomers of preferably greater than 5:1, more preferably greater than 10:1 and most preferably greater than 25:1 can be obtained by the processes of this invention. The processes of this invention occur at reaction rates suitable for commercial exploitation.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include epoxidation, ozonolysis, halogenation, hydrohalogenation, hydrogenation, esterification, oxidation of alcohols to aldehydes, ketones and/or carboxylate derivatives, N-alkylation of amides, addition of aldehydes to amides, nitrile reduction, acylation of alcohols by esters, acylation of amines and the like. To further illustrate, exemplary classes of pharmaceuticals which can be synthesized by a scheme including the subject stereoselective reaction are cardiovascular drugs, nonsteroidal antiinflammatory drugs, central nervous system agents, and antihistaminics.

III. Catalysts

The catalysts employed in the subject method involve chiral complexes which provide controlled steric environments for asymmetric nucleophilic addition reactions. In general, catalysts intended by the present invention can be characterized in terms of a number of features. For instance, a salient aspect of each of the catalysts contemplated by the instant invention concerns the use of metalloligands which provide a rigid or semi-rigid environment near the catalytic site of the molecule. This feature, through imposition of structural rigidity on the chelated metal, can be used to establish selective approach of the substrate to the catalytic site and thereby induce stereoselectivity and/or regioselectivity in a nucleophilic addition reaction. Moreover, the ligand preferably places a restriction on the coordination sphere of the metal.

Another aspect of the catalyst concerns the selection of metal atoms for the catalyst. In general, any main-group metal may be used to form the catalyst, e.g., a metal selected from one of Groups 1, 2, 12, 13, or 14 of the periodic table. However, in preferred embodiments, the metal will be selected from Groups 12, 13, or 14. For example, suitable metals include Li, Na, K, Rb, Be, Mg, Ca, Sr, Zn, Cd, Hg, B, Al, Ga, In, Si, Ge, and Sn. Particularly preferred metals are from groups 13 or 14, especially Al(III).

A. Chiral Tetradentate Catalysts

Consistent with these desirable features, one class of particularly preferred chiral catalysts provide a chiral tetradentate ligand which coordinates a main-group metal in a substantially square planar or square pyramidal geometry, though some distortion to these geometries is contemplated. Restated, these square geometries refer to tetradentate ligands in which the Lewis basic atoms lie substantially in the same plane, with the metal also in that plane (square planar), or above or below that plane (square pyramidal).

Preferred square tetradentate catalysts which may be employed in the subject reactions can be represented by the general formula 100:

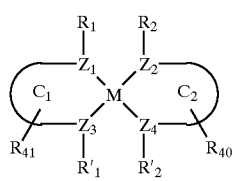

wherein $Z_1$, $Z_2$, $Z_3$ and $Z_4$ each represent a Lewis base, such as selected from the group consisting of nitrogen (e.g., imines, amines and amides), oxygen, phosphorus (e.g., phosphines or phosphinites), arsenic (arsines) and sulfur.

The $C_1$ moiety (taken with $Z_1$, $Z_3$ and M) and the $C_2$ moiety, (taken with $Z_2$, $Z_4$ and M) each, independently, form a heterocyclic ring. It will be understood that while the $C_1$ and $C_2$ structures depicted in the above formula may not formally be covalently closed rings for lack of a covalent bond with the metal M, for purposes of this disclosure, this and similar structures involving the metal catalyst atom M will nevertheless be referred to as heterocyclic rings, and substituents thereof will be referenced relative to heterocycle nomenclature (e.g., "fused rings" or "bridged rings"). In addition to substitutions at $R_1$, $R_2$, $R'_1$ and $R'_2$, the $C_1$ and $C_2$ ring can of course be substituted as appropriate at other ring positions, as illustrated by $R_{40}$ and $R_{41}$. Moreover, it will be appreciated that in certain embodiments two or more substituents of $C_1$ can be covalently bonded to each other to provide a fused ring or bridged ring including the $C_1$ ring atoms. Similar structures can be provided on the $C_2$ ring.

Accordingly, in the illustrated structure 100, $R_1$, $R_2$, $R'_1$ and $R'_2$ each independently are absent, or represent some substitution, as permitted by valence requirements, of the Lewis basic atoms, which substitution may be with hydrogen, halogens, alkyls, alkenyls, alkynyls, hydroxyl, alkoxyl, silyloxy, amino, nitro, thio amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ substituents taken together can form a bridging substituent; with the proviso that at least one of $R_1$, $R'_1$, and $R_{41}$ forms a bridging substituent with at least one of $R_2$, $R'_2$ and $R_{40}$ in order to provide $C_1$ and $C_2$ as a tetradentate; $R_7$ represents an aryl, a cycloalkyl, a cycloalkenyl, a heterocycle or a polycycle, and m is zero or an integer in the range of 1 to 8.

While the actual substituents of $C_1$ and $C_2$ can vary widely as necessary for a particular reaction scheme, one important proviso is that at least one substituent of $C_1$ must form a covalent bond with at least one substituent of $C_2$ in order to provide a tetradentate ligand which forms a square complex with M. That is, the ligand is a bridged cycle or polycycle which includes $C_1$ and $C_2$. Furthermore, in order for the catalyst to be chiral, e.g., to be capable of catalyzing stereoselective reactions, $R_1$, $R_2$, $R'_1$, $R'_2$ and other substituents of $C_1$ and $C_2$ are selected to provide at least one stereogenic center or an axis of dissymmetry, e.g. such that the ligand is asymmetric.

In the general structure 100, M represents a main-group metal of Groups 1, 2, 12, 13, or 14 of the periodic table. In the most preferred embodiments, M will be selected from the group of late main-group metals, e.g., from the Group 12, 13, or 14 metals. Even more preferably, M will be Al(III). Moreover, the metal can be coordinated with a counteranion or a nucleophile.

Exemplary catalysts of this class are comprised of ligands derived from, for example, salens, porphyrins, crown ethers, azacrown ethers, cyclams, phthalocyanines, and the like.

In a particularly preferred embodiment, the subject reactions use a chiral catalyst having a metal ion complexed via an imine of a chiral ligand, preferably a diimine bridge. Accordingly, such variants of structure 100 can be provided in embodiments wherein any one or more of the Lewis bases is an imine, with metallo-Schiff base forms of imines being highly preferred.

To further illustrate, a tetradentate catalyst useful in the subject method can be derived using chiral salen or salen-like ligands (hereinafter "salenates"). The asymmetric metallosalenate catalysts offer a distinct advantage over many other chiral tetradentate catalyts, such as the metalloporphyrinates described infra, in that the salenate ligand can have stereogenic centers located just two bond lengths away from the metal. This proximity of the chiral centers to the reactive site can yield a high degree of stereoselectivity.

As disclosed herein, salen complexes are highly effective catalysts for asymmetric nucleophilic addition reactions. This group of reactions is notable not only for its high stereoselectivity-enantioselectivity, diastereoselecivity, etc.—and for the utility of its products, but also for its remarkable efficiency as a catalytic process.

Moreover, the synthesis of chiral salenates is well characterized in the art, with more than 150 different chiral metallosalenates having been reported in the literature (see, for review, Collman et al. (1993) Science 261:1404–1411). These ligands are easily and inexpensively synthesized on large scale starting from readily available materials, as described in Larrow et al., *J Org Chem* (1994) 59:1939–1942. Importantly, the general familiarity and ease of synthesis of metallosalenates permits the substituents to be readily varied in a systematic fashion in order to adjust the steric or electronic characteristics of the ligand. This feature makes possible the synthesis of ligands which are optimized for particular types of reaction or substrate. It has been found that such steric and electronic "tuning" (described infra) of the catalysts can have significant effects on the yield and e.e. of products formed in asymmetric reactions. In particular, the use of bulky blocking substituents is desirable to achieve high product e.e. in the asymmetric nucleophilic additions. Furthermore, the stereogenic moiety can easily be modified to improve enantioselectivity.

In general, the salenate ligands which are useful in the subject method as chiral metallosalenate catalysts can be characterized as two substituted β-iminocarbonyls which are linked to form a tetradentate ligand having at least one stereogenic center. In an exemplary embodiment, a metallosalenate catalyst useful in the asymmetric nucleophilic addition processes of the present invention can be represented by a metal complex with two substituted β-iminocarbonyls having the general formula:

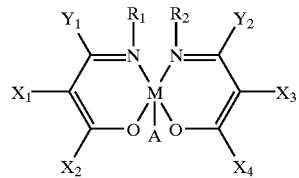

102 in which
the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$,
or any two or more of the substituents taken together form a carbocycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$ and $X_2$ representing different ends of a single substituent,
with the proviso that at least one of $R_1$, $Y_1$, $X_1$ and $X_2$ is covalently bonded to at least one of $R_2$, $Y_2$, $X_3$ and $X_4$ to provide the β-iminocarbonyls as a tetradentate ligand;

$R_7$ represents an aryl, a cycloalkyl, a cycloalkenyl, a heterocycle, or a polycycle;

m is zero or an integer in the range of 1 to 8;

M represents a main-group metal; and

A represents a counterion or a nucleophile;
wherein each of of the substituents of the β-iminocarbonyls, e.g., $R_1$, $R_2$, $Y_1$, $Y_2$, $X_1$, $X_2$, $X_3$ and $X_4$, are selected such that the catalyst is asymmetric.

The choice of each of $R_1$, $R_2$, $Y_1$, $Y_2$, $X_1$, $X_2$, $X_3$ and $X_4$ is also dependent on electronic and steric considerations, e.g., the tuning of the catalyst for a particular set of substrates, as well as the solvent system in which the reaction is to be carried out.

The chirality of the salenate ligand may be the result of the presence of one or more chiral atoms (e.g. carbon, sulfur, phosphorus, or other atoms capable of chirality), or may be the result of an axis of asymmetry due to restricted rotation, helicity, molecular knotting or chiral metal complexation. In preferred embodiments, the chiral ligand has at least one chiral atom or axis of asymmetry due to restricted rotation. Further guidance respecting the particular choice of the substituents is set out herein.

In preferred embodiments, the choice of $R_1$, $R_2$, $X_1$, $X_2$, $X_3$ and $X_4$ yield a class of chiral catalysts which are represented by the general formula:

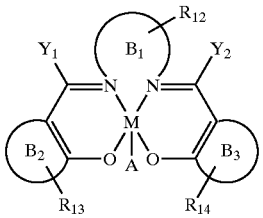

104 in which the $B_1$ moiety represents a diimine bridge, e.g. a bridging substituent which links the imino nitrogens of each β-iminocarbonyl, and preferably contains at least one chiral center of the salen ligand. For example, $B_1$, taken together with the metal-coordinating imines of the β-iminocarbonyl, can represent the diimine of an alkyl, an alkenyl, an alkynyl, or the diimine of —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfur, a sulfonyl, a selenium, or an ester; each of $B_2$ and $B_3$ independently represent rings selected from a group consisting of cycloalkyls, cycloalkenyls, aryls, and heterocycles, which rings comprise from 4 to 8 atoms in a ring structure. The substituents $R_{12}$, $R_{13}$ and $R_{14}$ each independently are absent, or represent one or more covalent substitutions of $B_1$, $B_2$ and $B_3$ with halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH2)_m$—$R_7$ (the substituent $R_{12}$ occuring on one or more positions of —$R_{15}$—$R_{16}$—$R_{17}$—); $R_7$ represents an aryl, a cycloalkyl, a cycloalkenyl, a heterocycle, or a polycycle; m is zero or an integer in the range of 1 to 8. Moreover, any two or more of the $R_{12}$, $R_{13}$, $R_{14}$, $Y_1$ and $Y_2$ substituted taken together can form bridging substituents to bridge the two β-iminocarbonyls and/or bridge different portions of the same β-iminocarbonyl. As above, in order to provide for a chiral catalyst, the choice of $B_2$ and $B_3$ (including their substituents) and/or the choice of substituents on $B_1$ (e.g., $B_1$ has a stereogenic center) is made to establish a chiral ligand. A represents a nucleophile or counterion.

In particular, as described in the appended examples, the salenate ligand can be derived from condensation of a substituted salicylaldehyde with a substituted diamine, preferably one stereoisomer of a chiral diamine, and then reacted with a desired metal to form a salen (N,N'-bis (salicylideneamino)alkyl)metal complex. An exemplary reaction for generating the salen ligand is based on Zhang and Jacobsen *J Org Chem* (1991) 56:2296–2298, and Jacobsen et al. PCT WO93/03838, and comprises:

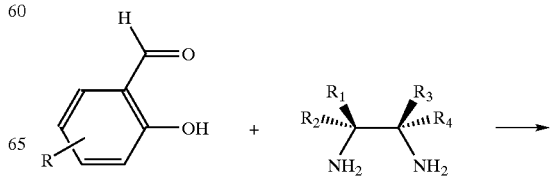

-continued

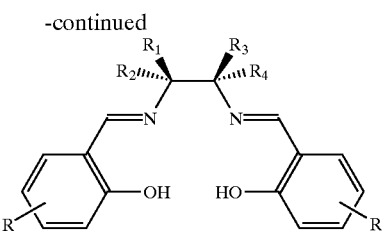

Utilizing this reaction scheme and others generally known in the art can provide a class of salens represented by the general formula 106:

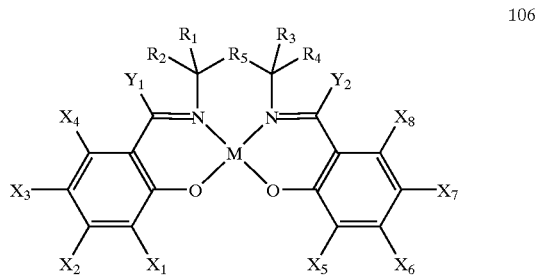

106 in which
each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_7$;
or any two or more of the substituents taken together form a carbocyle or heterocycle having at least 4 atoms in the ring structure;
$R_7$ represents an aryl, a cycloalkyl, a cycloalkenyl, a heterocycle or a polycycle;
m is zero or an integer in the range of 1 to 8; and
M represents a main-group metal;
wherein
if $R_5$ is absent, at least one of $R_1$ and $R_2$ is covalently bonded to at least one of $R_3$ and $R_4$; and the substituents of the salenate ligand are selected such that the salenate has at least one stereogenic center, e.g., is asymmetric. Moreover, the metal can be coordinated with a counterion (as in the aged catalyst described below).

With respect to generating a chiral ligand, it is important to note when selecting particular substituents that the salenate ligand has a potential catalytic site on both "sides" of the catalyst, e.g., relative to the plane of the four coordinating atoms of the ligand. Accordingly, when selecting the appropriate substituents for the β-iminocarbonyls in the above embodiments, it is important that either (1) both sides of the catalyst have stereogenic centers which effect identical stereoselectivity, or (2) the side having a stereogenic center of appropriate stereoselectivity is accessible while the other side has a blocking structure which substantially impairs approach to the metal atom on that side.

The first of these options is preferred. In other words, it is preferred to have at least one stereogenic center on each side of the salenate ligand, each having the same absolute (R or S) configuration. For example, (R,R)-1,2-Diphenyl-1,2-bis(3-tert-butylsalicylideamino)ethane, described in Example 1, contains two stereogenic centers on the diimine bridge which give rise to identical stereoselective faces on each side of the catalyst. This C$_2$-symmetric catalyst has the advantage of not being susceptible to "leakage" reactions because substrate approach, albeit constrained, may occur from either face without loss of selectivity.

In contrast, control of the reactivity of a "mono-faced" catalyst can be accomplished by sterically hindering substrate approach to the undesired face. For instance, the salenate (R)-2-phenyl-1,2-bis(3-tert-butylsalicylideamino)ethane, e.g., formula 106 wherein $R_1$, $R_2$ and $R_3$ are protons, and $R_4$ is a phenyl, has two non-equivalent faces in terms of enantioselectivity. Accordingly, derivatizing the salenate ligand with a group which blocks access to the "free" face (e.g., the face having both a C1 and C2 proton of the diimine) can establish the ligand as a chiral catalyst with one enantiotopic face. For instance, a "picnic basket" form of the ligand can be generated wherein the phenyl moiety of the diimine bridge is on the "frontside" of the catalyst, and $X_4$ and $X_8$ are covalently linked to form a bridge on the "backside" of the catalyst, which bridge substitution precludes access to the metal ion from the backside. Those skilled in the art will recognize other single- and double-sided embodiments (see, for example, Collman et al. (1993) Science 261:1404).

The synthetic schemes for metallosalenates, or precursors thereof, which may be useful in the present method can be adapted from the literature. For example, see Zhang et al. (1990) J Am Chem Soc 112:2801; Zhang et al. (1991) J Org Chem 56:2296; Jacobsen et al. (1991) J Am Chem Soc 113:7063; Jacobsen et al. (1991) J Am Chem Soc 113:6703; Lee et al. (1991) Tetrahedron Lett 32:5055; Jacobsen, E. N. In Catalytic Asymmetric Synthesis, Ojima, I., Ed., VCH: New York, 1993, chapter 4.2; E. N. Jacobsen PCT Publications WO81/14694 and WO93/03838; Larrow et al. (1994) J Am Chem Soc 116:12129; Larrow et al. (1994) J Org Chem 59:1939; Irie et al. (1990) Tetrahedron Lett 31:7345; Irie et al. (1991) Synlett 265; Irie et al. (1991) Tetrahedron Lett 32:1056; Irie et al. (1991) Tetrahedron Asymmetry 2:481; Katsuki et al. U.S. Pat. No. 5,352,814; Collman et al. (1993) Science 261:1404; Sasaki et al. (1994) Tetrahedron 50:11827; Palucki et al. (1992) Tetrahedron Lett 33:7111; and Srinivasan et al. (1986) J Am Chem Soc 108:2309. Exemplary salenate ligands described in the above references are illustrated below, as well as in the appended examples [Ph=phenyl; tBu=tert-butyl].

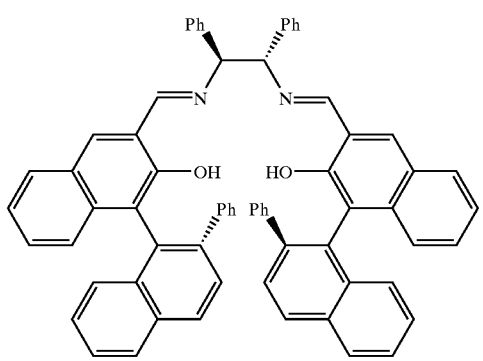

-continued

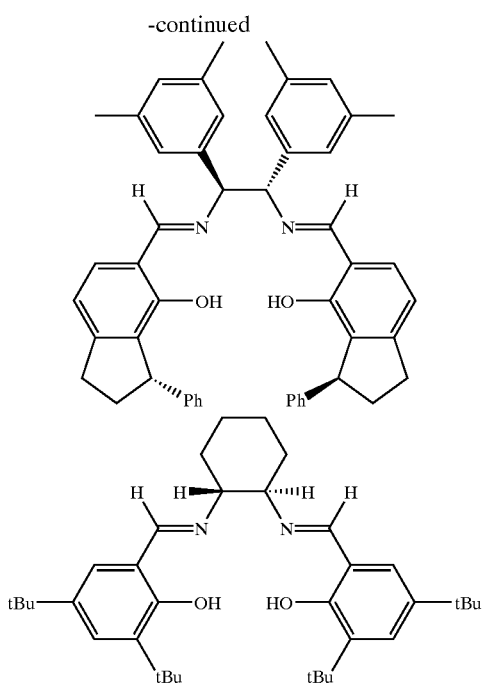

In yet another embodiment of the subject method, the tetradentate catalyst of formula 100 is derived as a chiral tetradentate ligand represented, with the metal atom, by the general formula:

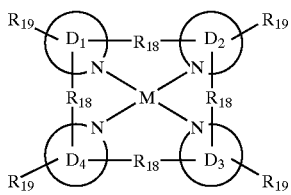

in which
$D_1$, $D_2$, $D_3$ and $D_4$ each represent heterocycles, such as pyrrole, pyrrolidine, pyridine, piperidine, imidazole, pyrazine, or the like;
each $R_{18}$ occurring in the structure represents a bridging substituent which links adjacent heterocycles, and preferably contains at least one stereogenic center of the ligand. For example, each $R_{18}$, represents an alkyl, an alkenyl, an alkynyl, or —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfer, a selenium, or an ester;
each $R_{19}$, independently, is absent or represents one or more substituents of the heterocycle to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, and —$(CH_2)_m$—$R_7$;
or any two or more of the $R_{18}$ and $R_{19}$ substituents are covalently linked to form a bridge substitution;

$R_7$ represents an aryl, a cycloalkyl, a cycloalkenyl, a heterocycle or a polycycle;
m is zero or an integer in the range of 1 to 8; and
M represents a main-group metal,
wherein each of the substituents $R_{18}$ and $R_{19}$ are selected such that the catalyst is asymmetric, e.g., the catalyst contains at least one stereogenic center. The metal will generally be coordinated with a counterion (as in the aged catalyst described below).

In preferred embodiments, $D_1$–$D_4$ are substituted pyrroles, and the catalyst is a chiral porphyrin or porphyrin-like ligand (hereinafter "porphyrinates"). As with the salenate ligands above, the synthesis of a vast number of porphyrinates has been reported in the literature. In general, most chiral porphyrins have been prepared in three ways. The most common approach involves attaching chiral units to preformed porphyrins such as amino- or hydroxy-substituted porphyrin derivatives (Groves et al. (1983) *J Am Chem Soc* 105:5791). Alternatively, chiral substituents can be introduced at the porphyrin-forming stage by allowing chiral aldehydes to condense with pyrrole (O'Malley et al. (1989) *J Am Chem Soc* 111:9116). Chiral porphyrins can also be prepared without the attachment of chiral groups. Similar to the bridged enantiotopic faces described for the salenates above, bridged porphyrinates can be generated by cross-linking adjacent and/or opposite pyrrolic positions and then separating the resulting mono-faced enantiomers with preparative HPLC using a chiral stationary phase (Konishi et al. (1992) *J Am Chem Soc* 114:1313). Ultimately, as with the generation of chiral salenate ligands, the resulting porphyrinate must have no mirror plane in order to be considered chiral.

With reference to formula 100, it will be understood that metalloporphyrinate catalysts, in addition to being represented by formula 108. can be represented generally by the compound of formula 100 when each of $Z_1$, $Z_2$, $Z_3$ and $Z_4$ represent nitrogen, and $C_1$ and $C_2$ along with their substituents (including $R_1$, $R'_1$, $R_2$, $R'_2$) form four substituted pyrrole rings which include $Z_1$, $Z_2$, $Z_3$ and $Z_4$. To complete the square tetradentate ligand, each pyrrole ring is covalently attached to the two adjacent pyrrole rings.

In preferred embodiments, the metalloporphyrinate catalyst is represented by the general formula 110:

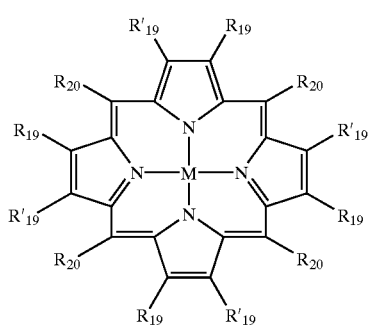

in which
each $R_{20}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;
each $R_{19}$ and $R'_{19}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

or any two R$_{19}$ and R'$_{19}$ substituents on the same pyrrole can be taken together to form a fused carbocycle or fused heterocycle having from 4 to 7 atoms in the ring structure;

or any two or more of the R$_{19}$, R'$_{19}$ and R$_{20}$ substituents are covalently cross-linked to form a bridging substituent;

R$_7$ represents an aryl, a cycloalkyl, a cycloalkenyl, a heterocycle or a polycycle;

m is zero or an integer in the range of 1 to 8; and

M represents a main-group metal, wherein the substituents R$_{19}$, R'$_{19}$ and R$_{20}$ are selected such that the catalysthas at least one stereogenic center, e.g., is asymmetric. The metal will generally be coordinated with a counterion (as in the aged catalyst described below).

As with the salenate ligands previously described, it is possible to sterically and electronically "tune" the porphyrin ligands to optimize reaction yield and e.e. Examples of suitable porphyrin ligands and synthesis schemes can be adapted from the art. For example, see Chang et al. (1979) *J Am Chem Soc* 101:3413; Groves et al. (1989) *J Am Chem Soc* 111:8537; Groves et al. (1990) *J Org Chem* 55:3628; Mansuy et al. (1985) *J Chem Soc Chem Commun* p155; Nauta et al. (1991) *J Am Chem Soc* 113:6865; Collman et al. (1993) *J Am Chem Soc* 115:3834; and Kruper et al. (1995) *J Org Chem* 60:725.

Still another class of the tetradentate catalysts represented by the general formula 100 and which are useful in the present asymmetric synthesis reactions can be represented by the formula 112:

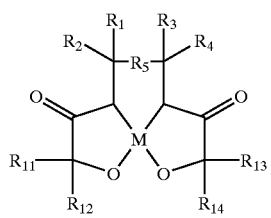

in which each of the substituents R$_1$, R$_2$, R$_3$, R$_4$, R$_5$, R$_{11}$, R$_{12}$, R$_{13}$ and R$_{14}$, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

or any two or more of the substituents taken together form a carbocycle or heterocycle having at least 4 atoms in the ring structure;

R$_7$ represents an aryl, a cycloalkyl, a cycloalkenyl, a heterocycle or a polycycle;

m is zero or an integer in the range of 1 to 8; and

M represents a main-group metal;

wherein if R$_5$ is absent, at least one of R$_1$ and R$_2$ is covalently bonded to at least one of R$_3$ and R$_4$, and the substituents are selected such that the catalyst is asymmetric. The metal will generally be coordinated with a counterion (as in the aged catalyst described below). Exemplary catalysts of formula 112 include:

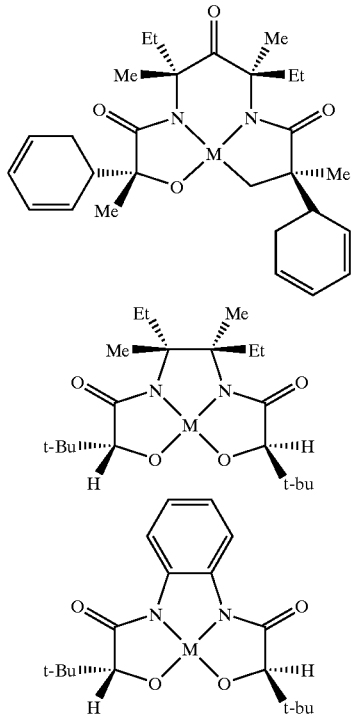

Three Specific Formulations of 112

The synthesis of these and other related catalyst can be adapted from the literature. See, for example, Ozaki et al. (1990) *J Chem Soc Perkin Trans*2:353; Collins et al. (1986) *J Am Chem Soc* 108:2088; and Brewer et al. (1988) *J Am Chem Soc* 110:423.

In yet another embodiment, the tetradentate catalysts of formula 100 can be chosen from the class of azamacrocycle having a ligand represented by the general formula 114:

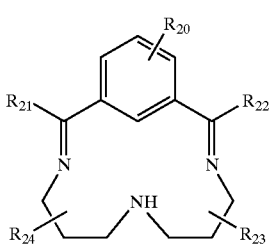

wherein

R$_{21}$, and R$_{22}$ each represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

R$_{20}$ is absent or represents one or more substituents of the pyridine to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

$R_{23}$ and $R_{24}$ each independently are absent or represent one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ and $R_{24}$ substituents are covalently linked to form a bridging substituent;

$R_7$ represents an aryl, a cycloalkyl, a cycloalkenyl, a heterocycle or a polycycle; and m is zero or an integer in the range of 1 to 8, wherein the substituents $R_{20}$, $R_{21}$, $R_{22}$, $R_{23}$ and $R_{24}$ are selected such that the catalyst is asymmetric.

One advantage to this class of tetradentate catalysts, like the salenates, derives from the fact that the ligand provides a metallo-shiff base complex. Furthermore, stereogenic centers can be sited within two bond lengths of the metal center. Exemplary ligands of formula 114 include:

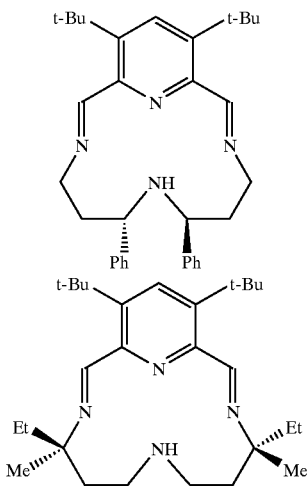

Two Specific Formulations of 114

The synthesis of these and other embodiments of 114 are described in Prince et al. (1974) *Inorg Chim Acta* 9:51–54, and references cited therein.

Yet another class of tetradentate ligands of the subject method are the cyclams, such as represented by the general formula 116:

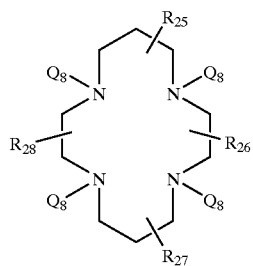

116 in which each of the substituents $Q_8$ indpendently, are absent or represent hydrogen or a lower alkyl, and each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$; or any two or more of the substituents taken together form a bridging substituent; $R_7$ represents an aryl, a cycloalkyl, a cycloalkenyl, a heterocycle , or a polycycle; and m is zero or an integer in the range of 1 to 8. Wherein the substituents are selected such that the catalyst is asymmetric. Exemplary embodiments and synthesis schemes for chiral cyclams useful in the present invention can be adapted from the art. See, for example, the Burrows et al. U.S. Pat. No. 5,126,464, Kimura et al. (1984) *Inorg Chem* 23:4181; Kimura et al. (1984) *J Am Chem Soc* 106: 5497; Kushi et al. (1985) *J Chem Soc Chem Commun* 216; Machida et al. (1986) *Inorg Chem* 25:3461; Kimura et al. (1988) *J Am Chem Soc* 110:3679; and Tabushi et al. (1977) *Tetrahedron Lett* 18:1049.

B. Chiral Tridentate Catalysts

In yet another embodiment of the subject method, the chiral catalyst which is provided in the reaction is from a class of chiral catalyst having a tridentate ligand which coordinates a main-group metal in a substantially planar geometry, though as above some distortion to this geometry is contemplated. Accordingly, this planar geometry refers to tridentate ligands in which the Lewis basic atoms lie in the same plane, with the metal also in that plane, or slightly above or below that plane.

Preferred planar tridentate catalysts which may be employed in the subject reactions can be represented by the general formula 140:

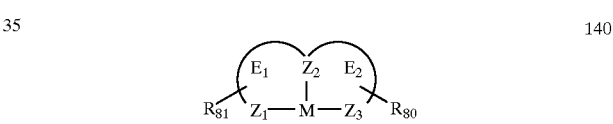

140 wherein $Z_1$, $Z_2$, and $Z_3$ each represent a Lewis base, such as selected from the group consisting of nitrogen, oxygen, phosphorus, arsenic and sulfur; the $E_1$ moiety, taken with $Z_1$, $Z_2$ and M, and the $E_2$ moiety, taken with $Z_2$, $Z_3$ and M, each, independently, form heterocycles; $R_{80}$ and $R_{81}$, each independently are absent, or represent one or more covalent substitutions of $E_1$ and $E_2$ with an organic or inorganic substituent permitted by valence requirements of the ring atom to which it is attached, or any two or more of the $R_{80}$ and $R_{81}$ substituents taken together form a bridging substituent; and M represents a main-group metal, wherein each $R_1$, $R_2$, $R'_1$, $R'_2$ $R_{80}$ and $R_{81}$ substituents are selected to provide at least one stereogenic center in said tridentate ligand. In preferred embodiments, each $R_{80}$ and $R_{81}$ occurring in 140 independently represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—R7; $R_7$ represents an aryl, a cycloalkyl, a cycloalkenyl, a heterocycle or a polycycle; and m is zero or an integer in the range of 1 to 8. The metal will generally be coordinated with a counterion (as in the aged catalyst described below).

For example, a chiral tridentate catalyst useful in the subject stercoselective reactions can have a ligand represented by the general formula 142 and 144:

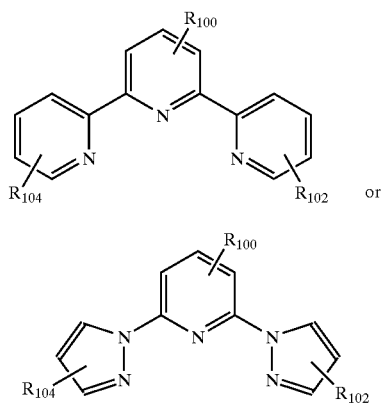

142

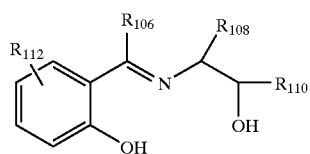

144 wherein each of $R_{100}$, $R_{102}$ and $R_{104}$ each independently are absent, or represent one or more covalent substitutions of heterocycle to which it is attached, or any two or more of the substituents taken together form a bridging substituent; wherein each $R_{100}$, $R_{102}$ and $R_{104}$ substituents, if present, can be selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. Again, the substitution of 142 is intended to provide at least one stereogenic center in the tridentate ligand. Exemplary embodiments of the 2,2':6', 2"-terpyridine ligands 142 and their synthesis can be adapted from, for example, Potts et al. (1987) *J Am Chem Soc* 109:3961; Hadda et al. (1988) *Polyhedron* 7:575; Potts et al. (1985) *Org Synth* 66:189; and Constable et al. (1988) *Inorg Chim Acta* 141:201. Exemplary 2,6-bis(N-pyrazolyl) pyridine ligands 144 can be adapted from, for example, Steel et al. (1983) *Inorg Chem* 22:1488; and Jameson et al. (1990) *J Org Chem* 55:4992.

Yet another class of planar tridentate catalyst useful in the subject stereoselective reactions can have a ligand represented by the general formula 146:

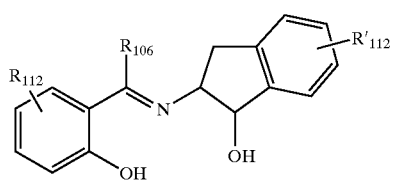

146 wherein each of $R_{106}$, $R_{108}$ and $R_{110}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{112}$ is absent or represent one or more covalent substitutions of the heterocycle to which it is attached; or any two or more of the $R_{106}$, $R_{108}$, $R_{110}$ and $R_{112}$ substituents taken together form a bridging substituent; $R_7$ represents an aryl, a cycloalkyl, a cycloalkenyl, a heterocycle or a polycycle; and m is zero or an integer in the range of 1 to 8. The choice of substitution of 146 is intended to enhance its chirality. Exemplary embodiments of the salicylaldehyde-derived ligands 146 and their synthesis can be adapted from, for example, Desimoni et al. (1992) *Gazzetta Chimica Italiana* 122:269.

In a preferred embodiment, the tridentate ligand is given by the general formula 150

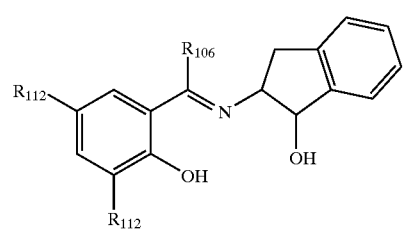

150 wherein $R_{106}$ represents a hydrogen, halogen, alkyl, alkenyl, alkynyl, hydroxyl, alkoxyl, silyloxy, amino, nitro, thiol amine, imine, amide, phosphonate, phosphine, carbonyl, carboxyl, silyl, ether, thioether, sulfonyl, selenoether, ketone, aldehyde, ester, or —$(CH_2)_m$—$R_7$; and each of $R_{112}$ and $R'_{112}$ is absent or represent one or more covalent substitutions of the heterocycle to which it is attached, such as designated for $R_{106}$; $R_7$ represents an aryl, a cycloalkyl, a cycloalkenyl, a heterocycle or a polycycle; and m is zero or an integer in the range of 1 to 8. For example, as described in the appended examples, a preferred salicylaldehyde-derived ligand is given by the general formula 152

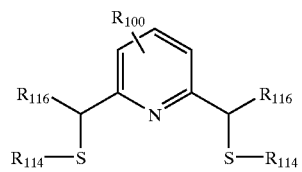

152 each $R_{112}$ being independently selected.

Still another class of planar tridentate catalyst useful in the subject stereoselective reactions can have a ligand represented by the general formula 148:

148 wherein $R_{100}$ is as described above, and each $R_{116}$ and $R_{114}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents taken together form a bridging substituent; $R_7$ represents an aryl, a cycloalkyl, a cycloalkenyl, a heterocycle or a polycycle; and m is zero or an integer in the range of 1 to 8. The choice of substitution of 148 is intended to provide at least one stereogenic center in the tridentate ligand. Exemplary embodiments of the salicylaldehyde-derived ligands 148 and their synthesis can be adapted from, for example, Marangoni et al. (1993) *Polyhedron* 12:1669.

C. Tuning the Catalysis

The ligand substituents are chosen to optimize the selectivity of the reaction and the catalyst stability. The exact mechanism of action of the metallosalenate-catalyzed nucleophilic addition reactions has not yet been precisely elucidated. However, the need for stereoselective non-bonded interactions between the substrate and catalyst is a feature of this catalyst and other chiral planar catalysts of the subject reaction. While not wishing to be bound by any particular theory, it is believed that the present nucleophilic addition reactions involve two factors largely responsible for induction of asymmetry by formation of stereospecific non-bonded pairs of catalyst and substrate, namely, steric and electronic interactions between a substrate and the ligand of the chiral catalyst. In general, "tuning" refers altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction. For instance, the choice of appropriate substituents as "blocking groups" enforces certain approach geometries and disfavors others.

Furthermore, the choice of substituent may also affect catalyst stability; in general, bulkier substituents are found to provide higher catalyst turnover numbers. It has been found that for the asymmetric epoxidation of olefins by Mn(salen) complexes, t-butyl groups (or other tertiary groups) are suitable bulky moieties for optimizing stereoselectivity and increasing catalyst turnover.

A preferred version of each of the embodiments described above provides a catalyst having a molecular weight less than 5,000 a.m.u., more preferably less than 3,000 a.m.u., and even more preferably less than 2,500 a.m.u. In another preferred embodiment, none of the substituents of the core ligand, or any molecule coordinated to the metal in addition to the ligand, have molecular weights in excess 1,000 a.m.u., more preferably they are less than 500 a.m.u., and even more preferably, are less than 250 a.m.u. The choice of substituent on the ligand can also be used to influence the solubility of the catalyst in a particular solvent system.

As mentioned in brief above, the choice of ligand substituents can also affect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl) on the ligand result in lower electron density of the ligand and metal center. The electron density of the ligand is important due to the possibility of interactions (such as π-stacking) with the substrate (see, e.g., Hamada et al. *Tetrahedron* (1994) 50:11827). The electron density at the metal center may influence the Lewis acidity of the metal. Choice of appropriate substituents thus makes possible the "tuning" of the reaction rate and the stereoselectivity of the reaction.

Substrates

Substrates which are useful in the present invention may be determined by the skilled artisan according to several criteria. In general, suitable substrates will have one or more of the following properties: 1) The substrate will be capable of participating in a nucleophilic addition reaction under the subject conditions; 2) Said nucleophilic addition reaction will yield a useful product; 3) The substrate will not react at undesired functionalities; 4) The substrate will react at least partly through a mechanism catalyzed by the chiral catalyst; 5) The substrate will not undergo significant further undesired reaction after reacting in the desired sense; 6) The substrate will not substantially react with or degrade the catalyst, e.g. at a rate greater than conversion of the substrate. It will be understood that while undesirable side reactions (such as catalyst degradation) may occur, the rates of such reactions can be manipulated through the selection of reactants and conditions; these manipulations will render the undesired side reaction(s) slow in comparison with the rate(s) of the desired reaction(s).

In certain embodiments, the reactive substrates may be contained in the same molecule, thereby resulting in an intramolecular nucleophilic addition reaction.

As discussed above, a wide variety of substrates are useful in the methods of the present invention. The choice of substrates will depend on factors such as the desired product, and the appropriate substrates will be apparent to the skilled artisan. It will be understood that the substrates preferably will not contain any interfering functionalities. In general, appropriate substrates will contain a reactive π-bond and/or a nucleophilic locus.

Reaction Conditions

The asymmetric addition reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the substrate, the catalyst, or the product. For example, the reaction temperature influences the speed of the reaction, as well as the stability of the reactants and catalyst. The reactions will usually be run at temperatures in the range of −78° C. to 100° C., more preferably in the range −30° C. to 50° C. and still more preferably in the range −30° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed. In certain embodiments, ethereal solvents are preferred.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. The partial pressure of the reactive gas may be from 0.1 to 1000 atmospheres, more preferably from 0.5 to 100 atm, and most preferably from about 1 to about 10 atm. In certain embodiments it is preferable to perform the reactions under an atmosphere of an inert gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion. In certain embodiments, particular orders of combination of substrate, nucleophile, catalyst, and solvent may result in increased yield of product, increased stereo- or regio-selectivity, and/or increased reaction rate.

The subject reactions can be conducted in a single reaction zone or in a plurality of reaction zones, in series or in parallel or they may be conducted batchwise or continuously in an elongated tubular zone or series of such zones. The materials of construction employed should be inert to the starting materials—substrate, nucleophile, catalyst, and solvent—during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glaas, glass-lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, derivativation with one or more of substituents of the ligand. The immobilized ligands can be complexed with the desired metal to form the chiral metallocatalyst. The catalyst, particularly the "aged" catalyst discussed herein, is easily recovered after the reaction as, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

Example 1

This example describes the enantioselective addition of HCN to imines (the Strecker reaction) catalyzed by the chiral (salen)Al(III) complex 8. In the first successful application of main-group (salen)metal complexes in asymmetric catalysis, excellent enantioselectivities are achieved in the hydrocyanation of a range of aryl substituted imines. The applicability of this methodology to the practical synthesis of enantiomerically pure amino acid derivatives is illustrated in a synthesis of enantiopure (S)-2-naphthylglycine methyl ester on a 6 mmol scale.

The addition of cyanide to imines (the Strecker reaction)[1] constitutes one of the most direct and viable strategies for the asymmetric synthesis of α-amino acid derivatives. Significant progress has been made in the development of stereoselective versions of this reaction using imines bearing covalently attached chiral auxiliaries.[2] However, despite the obvious practical potential of an enantioselective catalytic version of the Strecker reaction, only limited success has been attained to this end.[3] In this example, we describe the first example of a metal catalyzed enantioselective Strecker reaction using a chiral (salen)Al(III) complex.

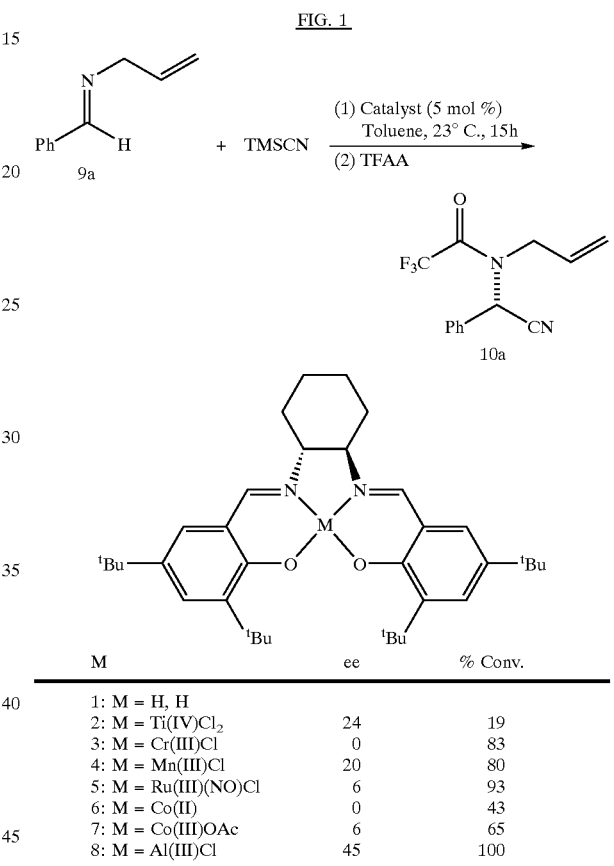

FIG. 1

| M | ee | % Conv. |
|---|---|---|
| 1: M = H, H | | |
| 2: M = Ti(IV)Cl$_2$ | 24 | 19 |
| 3: M = Cr(III)Cl | 0 | 83 |
| 4: M = Mn(III)Cl | 20 | 80 |
| 5: M = Ru(III)(NO)Cl | 6 | 93 |
| 6: M = Co(II) | 0 | 43 |
| 7: M = Co(III)OAc | 6 | 65 |
| 8: M = Al(III)Cl | 45 | 100 |

Chiral (salen)-metal complexes catalyze an array of asymmetric nucleophile-electrophile reactions including TMSN$_3$[4] and carboxylic acid additions to meso epoxides,[5] hetero Diels-Alder,[6] and TMSCN addition to aldehydes.[7] Also, (salen)Cr and (salen)Co complexes have proven remarkably effective in the kinetic resolutions of terminal epoxides with TMSN$_3$[8] and H$_2$O.[9] Encouraged by the proven effectiveness of aldehydes and epoxides as electrophiles in (salen)-metal catalyzed enantioselective reactions, we evaluated the possibility of extending the scope of these catalysts to asymmetric transformations of imines. To this end, we screened a series of metal complexes of the readily available salen ligand 1 for catalysis of the addition of TMSCN to N-allyl benzaldimine (9a). Complexes of Ti, Cr, Mn, Co, Ru and Al were all found to catalyze the reaction at room temperature with varying degrees of conversion and enantioselectivity.[10] The best result obtained was with the Al complex 8,[11,12] which led to complete substrate conversion and afforded product 10a in 45% ee. Interestingly, no reaction was observed under strictly anhydrous conditions in the reaction catalyzed by 8, suggesting that the reacting species is HCN rather than TMSCN. At room temperature, the uncatalyzed reaction between HCN and 9a is quite rapid, but it is completely suppressed at −70 °C. At this lower temperature, the reaction of 9a and HCN[13] (1.2 equiv) catalyzed by 8 was complete within 15 h, and afforded 10a in 91% isolated yield and 95% ee (Table 1, entry a).[14,15]

TABLE 1

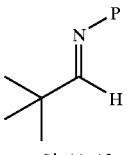

| Entry | | R | % yield[a] | % ee[b] |
|---|---|---|---|---|
| a | 9a | Ph | 91 | 95 |
| b | 9b | p-CH$_3$OC$_6$H$_4$ | 93 | 91 |
| c | 9c | p-CH$_3$C$_6$H$_4$ | 99 | 94 |
| d | 9d | p-ClC$_6$H$_4$ | 92 | 81 |
| e | 9e | p-BrC$_6$H$_4$ | 93 | 79 |
| f | 9f | 1-Napthyl | 95 | 93 |
| g | 9g | 2-Napthyl | 93(55)[c] | 93(>99)[c] |
| h | 9h | Cyclohexyl | 77 | 57 |
| i | 9i | t-Butyl | 69 | 37 |

[a]Isolated yield. Full Characterization of compounds 10a–i is provided in the Supporting Information.
[b]All ee's were determined by GC or HPLC chromatography using commercial chiral columns. See Supporting Information.
[c]After recrystallization from hexanes.

A variety of N-allyl imines were evaluated in the reaction catalyzed by 8 (Table 1). The products 10a–i were isolated as the (S)-trifluoroacetamides in good yield and moderate-to-excellent enantioselectivity. Substituted aryl imines (9a–g) were clearly the best substrates, affording very high levels of enantioselectivity (entries a–g). In contrast, alkyl substituted imines underwent addition of HCN with considerably lower ee's (entries h–i).

With the hope of improving the results obtainable with alkyl substituted imines, we evaluated the effect of the catalyst structure and the imine nitrogen substituent on reaction enantioselectivity. Extensive variation of the steric and electronic properties of the (salen)AlCl ligand structure failed to yield any improvement in reaction enantioselectivity over that obtained with catalyst 8. Several N-substituted imines of pivalaldehyde, an attractive starting material for the asymmetric synthesis of tert-leucine, were synthesized and screened (Table 2). Surprisingly, the N-substituent did not exert a very significant influence on the enantioselectivity of the reaction. Although only a marginal increase in ee was obtained with the N-benzyl derivative 11, enhancement of the enantiomeric purity to 97.5% was achievable with reasonably good recovery by recrystallization of the corresponding product 14.

TABLE 2

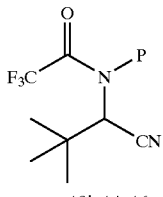

| | P | % yield | % ee |
|---|---|---|---|
| 10i | Allyl | 69 | 37 |
| 14 | Benzyl | 88(48)[a] | 49(97.5)[a] |
| 15 | p-methoxybenzyl | 67 | 44 |
| 16 | o-CH$_3$OC$_6$H$_4$ | 74 | 40 |

[a]After recrystallization from 1:10 EtOAc:hexanes

The principal synthetic utility of the asymmetric Strecker reaction is for the preparation of enantiomerically enriched α-amino acid derivatives. To illustrate the applicability of the present method, imine 9g was converted on 6 mmol scale to the amino methyl ester HCl salt 18, by means of a three step sequence requiring no chromatography (Scheme 1). With a reduced catalyst loading of 8 (2 mol %), the corresponding amino nitrile was still obtained in high yield and in 92% ee within 15 h. Hydrolysis of the hydrocyanation adduct with methanolic HCl at reflux produced the allyl protected amino ester 17 in 78% yield over two steps with no racemization. Deprotection was achieved by Pd(0)-catalyzed deallylation using dimethylbarbituric acid as an allyl scavenger[16] followed by recrystallization to afford 18 in 60% yield and in enantiomerically pure form (>99% ee).

Scheme 1

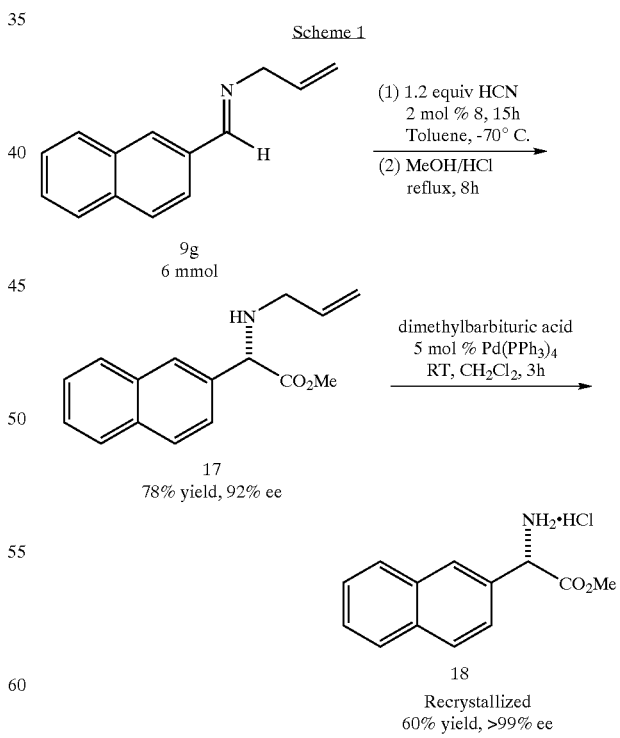

The asymmetric Strecker reaction catalyzed by 8 provides a straightforward entry into enantiomerically enriched α-amino acid derivatives using low catalyst loading from readily available substrate and catalyst precursors. The catalyst is easily prepared on large scale and appears to have an indefinite "shelf life" even when stored under ambient conditions. To our knowledge, this is the first instance in which a main group (salen)metal complex has been identified as a highly effective asymmetric catalyst. Experiments are underway to elucidate the mechanism of this new enantioselective transformation, and to establish to what extent this reaction is related mechanistically to other classes of (salen)metal catalyzed nucleophile-electrophile reactions.[17]

REFERENCES AND NOTES (1) Strecker, A. *Ann. Chem. Pharm.* 1850, 75, 27.
(2) (a) Williams, R. M. *Synthesis of Optically Active α-Amino Acids*; Pergamon: Oxford, 1989, Chap. 5 and references cited therein. (b) Williams, R. M.; Hendrix, J. A. *Chem. Rev.* 1992, 92, 889–917. (c) Duthaler, R. O. *Tetrahedron* 1994, 50, 1539.
(3) (a) Iyer, M. S.; Gigstad, K. M.; Namdev, N. D.; Lipton, M. *J. Am. Chem. Soc.* 1996, 118, 4910. (b) Sigman, M. S.; Jacobsen, E. N. *J. Am. Chem. Soc.*, in press.
(4) Martinez, L. E.; Leighton, J. L.; Carsten, D. H.; Jacobsen, E. N. *J. Am. Chem. Soc.* 1995, 117, 5897.
(5) Jacobsen, E. N.; Kakiuchi, F.; Konsler, R. G.; Larrow, J. F.; Tokunaga, M. *Tetrahedron Lett.* 1997, 38, 773.
(6) Schaus, S. E.; Branalt, J.; Jacobsen, E. N. *J. Org. Chem.* 1998, 63, 403.
(7) (a) Belokon, Y.; Flego, M.; Ikonnikov, N.; Moscalenko, M.; North, M.; Orizu, C.; Tararov, V.; Tasinazzo, M. *J. Chem. Perkin Trans. 1* 1997, 1293. (b) Belokon, Y; Ikonikov, N.; Moscalenko, M.; North, M.; Orlova, S.; Tararov, V.; Yashkina, L. *Tetrahedron: Asymmetry* 1996, 7, 85i.
(8) Larrow, J. F.; Schaus, S. E.; Jacobsen, E. N. *J. Am. Chem. Soc.* 1996, 118, 7420.
(9) Tokunaga, M.; Larrow, J. F.; Kakiuchi, F.; Jacobsen, E. N. *Science* 1997, 277, 936.
(10) The corresponding vanadyl, Fe(III), Ni(II), Cu(II) and Sn(IV) salen complexes were found to effect the reaction to less than 5% conversion.
(11) Catalyst Preparation (8): In a flamed dried 100 ml round bottom flask equipped with a stir bar, 1.52 g (2.78 mmol) of (R,R)-(−)-N, N'-bis(3,5-di-tert-butylsalicylidene)-1,2-cyclohexanediamine and 20 mL of $CH_2Cl_2$ (freshly distilled from $CaH_2$) were combined and stirred. At ambient temperature, 1.54 ml of diethyl aluminum chloride (1.8 M solution in toluene, 2.78 mmol) was added slowly to the stirring solution. After stirring for 2 h, the solvents were removed in vacuo and the resulting yellow solid was rinsed with 50 ml of hexanes. The solid was dried in vacuo to yield 8 (1.59 g, 95% yield ) as a yellow solid. mp>350° C. (dec); IR(KBr) 2966, 2953, 2867, 1640, 1544, 848 $cm^{-1}$; $^1H$ NMR (400 MHz, $C_6D_6$) δ 7.84 (s, 2H), 7.77 (s, 2H), 7.61 (s, 2H), 3.51 (m, 2H), 1.91 (s, 18H), 1.39 (s, 18H) 1.36 (m, 4H), 0.59 (m, 4H); $^{13}C$ NMR {$^1H$} (100 MHz, $CD_2Cl_2$) δ 162.7, 141.2, 139.3, 131.4, 128.7, 128.4, 118.7, 64.6 (broad), 35.9, 34.4, 31.6, 30.0, 28.2, 24.1; Anal calcd. for $C_{36}H_{52}AlClN_2O_2$: C, 71.20; H, 8.42; Al, 4.44; Cl, 5.84; N, 4.61. Found: C, 71.05; H, 8.63; Al, 4.49; Cl, 5.73; N, 4.56.
(12) For the synthesis of (salen)Al complexes see: (a) Dzugan, S. J.; Goedken, V. L. *Inorg. Chem.* 1986, 25, 2858. (b) Gurian, P. L.; Cheatham, L. K.; Ziller, J. W.; Barron, A. R. *J. Chem Soc., Dalton Trans.* 1991, 1449. (c) Atwood, D. A.; Jegier, J. A.; Rutherford, D. *Inorg. Chem.* 1996, 35, 63.
(13) Ziegler, K. In *Organic Synth. Coll. Vol.* 1, Gilman, H., Blatt, A. H. Eds.; Wiley: New York, 1932; p. 314. CAU- TION! Hydrogen Cyanide is a highly toxic and volatile compound that should be handled carefully to avoid inhalation.
(14) The direct product of HCN addition was observed to undergo racemization upon exposure to silica gel. The corresponding triflouroacetamde derivatives were found to be stable, so all yield and ee determinations were carried out on these derivatives.
(15) Representative Procedure: Synthesis of Compound 10a. In a flamed dried 5 mL round bottom flask equipped with a stir bar, 12 mg of 8 (5 mol %, 0.02 mmol) and 1.4 mL of toluene were combined. The reaction was stirred at ambient temperature until catalyst had completely dissolved. The reaction flask was cooled to −70° C. by means of a constant temperature bath and 1.2 equiv of HCN was added (0.59 mmol, 690 μL of a 0.85 M solution in toluene). After 5 min, 71 mg (0.49 mmol) of 9a was added in one portion via syringe. After 15 h, the reaction was quenched with 103 μL of trifluoroacetic anhydride (0.73 mmol, 1.5 equiv) and allowed to warm to ambient temperature. The solvents were removed in vacuo and the resulting residue was purified by flash chromatography (3:2 hexanes:$CH_2Cl_2$) to afford 10a as a clear oil (119 mg, 91% yield).
(16) Garro-Helion, F.; Merzouk, A.; Guibé, F. *J. Org. Chem.* 1993, 58, 6109.
(17) Hanson, K. B.; Leighton, J. L.; Jacobsen, E. N. *J. Am. Chem. Soc.* 1996, 44, 10924.

SUPPORTING INFORMATION

General procedure: The same procedure as outlined for 10a in footnote 15 of the main text of this example was followed for all compounds.

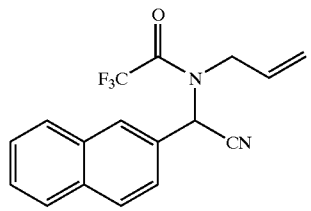

(10a): Product was obtained in 91% yield as a clear oil after purification by flash chromatography (3:2 hexanes:$CH_2Cl_2$) and in 95% ee by Chiral GC analysis (γ-TA, 112° C., 23 min, 3° C./min to 123° C., $t_r$(major)=21.5 min, $t_r$(minor)=23.9 min); $[α]_D^{23}$=57.7° (c=1.0, $CH_2Cl_2$); IR (thin film) 2936, 2249, 1701 $cm^{-1}$; $^1H$ NMR (400 MHz, $CDCl_3$) δ 7.45 (m, 5H), 6.65 (s, 1H), 5.66 (m, 1H), 5.19 (d, J=10.2 Hz, 1H), 5.13 (d, J=17.0 Hz, 1H) 4.15 (dd, J=4.7, 17.0 Hz, 1H), 3.91 (dd, J=6.0, 17.0 Hz, 1H); $^{13}C$ NMR {$^1H$} (100 MHz, $CDCl_3$) δ 157.9 (q, J=38 Hz), 131.1, 130.1, 130.0, 129.4, 127.8, 120.3, 117.5 (q, J=288 Hz), 115.2, 49.8, 48.6; HRMS m/z ($M+NH_4^+$) calcd 286.1167, obsd 286.1163.

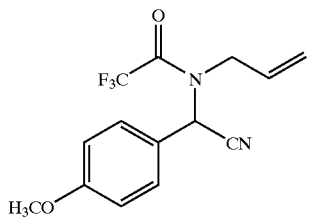

(10b): Product was obtained in 93% yield as a clear oil after purification by flash chromatography (3:2 hexanes:$CH_2Cl_2$)

and in 91% ee by Chiral HPLC analysis (Chiralcel AS, 5% IPA/Hexanes, 1 ml./min, t$_r$(major)=9.7 min, t$_r$(minor)=11.5 min); [α]$_D^{23}$=56.1° (c=1.0, CH$_2$Cl$_2$); IR (thin film) 2940, 1701, 1613 cm$^{-1}$; $^1$H NMR (400 MHz, CDCl$_3$) δ 7.36 (d, J=8.6 Hz, 2H), 6.94 (d, J=8.6 Hz, 2H), 6.57 (s, 1H), 5.65 (m, 1H), 5.19 (d, J=10.2 Hz, 1H), 5.14 (d, J=17.2 Hz, 1H), 4.15 (dd, J=4.2, 17.0 Hz, 1H), 3.87 (dd, J=6.2, 17.0 Hz, 1H), 3.83 (s, 3H); $^{13}$C NMR {$^1$H} (100 MHz, CDCl$_3$) δ 160.9, 157.8 (q, J=38 Hz), 131.4, 129.5, 121.9, 120.1, 117.5 (q, J=288 Hz), 115.6, 114.8, 55.5, 49.4, 48.3; HRMS m/z (M$^+$) calcd 298.0929, obsd 298.0936.

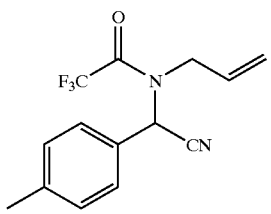

(10c): Product was obtained in 99% yield as a clear oil after purification by flash chromatography (3:2 hexanes:CH$_2$Cl$_2$) and in 94% ee by Chiral HPLC analysis (Chiralcel AS, 5% IPA/Hexanes, 1 ml./min, t$_r$(major)=5.5 min, t$_r$(minor)=7.6 min); [α]$_D^{23}$=42.4° (c=1.0, CH$_2$Cl$_2$); IR (thin film) 2930, 2249, 1703 cm$^1$; $^1$H NMR (400 MHz, CDCl$_3$) δ 7.32 (d, J=7.9 Hz, 2H), 7.24 (d, J=7.9 Hz, 2H), 6.60 (s, 1H), 5.68 (m, 1H), 5.20 (d, J=10.2 Hz, 1H), 5.14 (d, J=17.2 Hz, 1H), 4.14 (dd, J=4.8, 17.0 Hz, 1H), 3.86 (dd, J=6.5, 17.0 Hz, 1H), 2.39 (s, 3H);); $^{13}$C NMR {$^1$H} (100 MHz, CDCl$_3$) δ 157.4 (J=37 Hz), 140.3, 131.2, 130.0, 127.8, 127.0, 120.2, 117.4 (q, J=286 Hz), 115.4, 49.5, 48.4, 21.1; HRMS m/z (M$^+$) calcd 282.0980, obsd 282.0981.

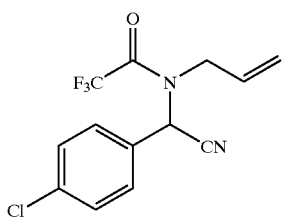

(10d) Product was obtained in 92% yield as a clear oil after purification by flash chromatography (3:2 hexanes:CH$_2$Cl$_2$) and in 81% ee by Chiral HPLC analysis (Chiralcel AS, 5% IPA/Hexanes, 1 ml./min, t$_r$(major)=5.9 min, t$_r$(minor)=8.4 min); [α]$_D^{23}$=45.9° (c=1.0, CH$_2$Cl$_2$); IR (thin film) 2936, 1703 cm$^{-1}$; $^1$H NMR (400 MHz, CDCl$_3$) δ 7.40 (m, 4H), 6.56 (s, 1H), 5.65 (m, 1H), 5.22 (d, J=10.4 Hz, 1H), 5.17 (d, J=17.2 Hz, 1H), 4.16 (dd, J=5.0, 17.0 Hz, 1H), 3.94 (dd, J=5.9, 17.0 Hz, 1H); $^{13}$C NMR {$^1$H} (100 MHz, CDCl$_3$) δ 157.4 (J=37 Hz), 136.3, 130.9, 129.6, 129.2, 128.8, 117.3 (q, J=286 Hz), 114.8, 49.4, 48.9; HRMS m/z(M$^+$) calcd 302.0434, obsd 302.0448.

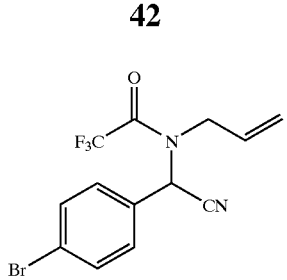

(10e): Product was obtained in 93% yield as a clear oil after purification by flash chromatography (3:2 hexanes:CH$_2$Cl$_2$) and in 79% ee by Chiral HPLC analysis (Chiralcel AS, 5% IPA/Hexanes, 1 ml./min, t$_r$(major)=6.2 min, t$_r$(minor)=8.1 min); [α]$_D^{23}$=48.0° (c=1.0, CH$_2$Cl$_2$); IR (thin film) 2936, 1701 cm$^{-1}$; $^1$H NMR (400 MHz, CDCl$_3$) δ 7.56 (d, J=8.4 Hz, 2H), 7.31 (d, J=8.4 Hz, 2H), 6.52 (s, 1H), 5.65 (m, 1H), 5.21 (d, J=10.2 Hz, 1H), 5.15 (d, J=17.1 Hz, 1H), 4.15 (dd, J=5.5, 17.0 Hz, 1H), 3.92 (dd, J=6.3, 17.0 Hz, 1H); $^{13}$C NMR {$^1$H} (100 MHz, CDCl$_3$) δ 157.7, 132.7, 131.0, 129.5, 124.5, 120.8, 117.4, 114.8, 114.5, 49.6, 49.0; HRMS m/z (M$^+$) calcd 345.9929, obsd 345.9931.

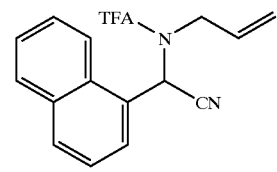

(10f): Product was obtained in 95% yield as a white solid after purification by flash chromatography (3:2 hexanes:CH$_2$Cl$_2$) and in 93% ee by Chiral HPLC analysis (Chiralcel AS, 5% IPA/Hexanes, 1 ml./min, t$_r$(major)=5.3 min, t$_r$(minor)=10.0 min); [α]$_D^{23}$=72.4° (c=1.0, CH$_2$Cl$_2$); mp 92–95° C.; IR (KBr) 2920, 1697 cm$^{-1}$; $^1$H NMR (400 MHz, CDCl$_3$) δ7.93 (m, 3H), 7.55 (m, 4H), 7.29 (s, 1H), 5.46 (m, 1H), 5.01 (d, J=10.2 Hz, 1H), 4.86 (d, J=17.1 Hz, 1H), 4.03 (dd, J=4.3, 17.1 Hz, 1H), 3.50 (dd, J=7.2, 17.1 Hz, 1H); $^{13}$C NMR {$^1$H} (100 MHz, CDCl$_3$) δ 157.4 (J=37 Hz), 133.6, 131.5, 131.0, 130.1, 129.3, 128.7, 128.0, 126.9, 124.4, 121.3, 119.7, 117.4 (q, J=286 Hz), 115.9, 47.9, 47.3; HRMS m/z (M$^+$) calcd 318.0980, obsd 318.0984.

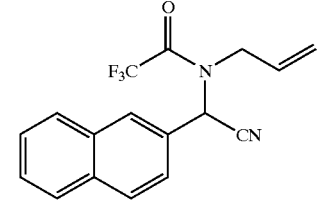

(10g): Product was obtained in 93% yield as a white solid after purification by flash chromatography (3:2 hexanes:CH$_2$Cl$_2$) and in 93% ee by Chiral HPLC analysis (Chiralcel AS, 5% IPA/Hexanes, 1 ml./min, t$_r$(major)=7.0 min, t$_r$(minor)=8.4 min). Recrystallization from a minimal amount of hexanes at 0° C. yielded 54% (from imine) of thin needles in >99% ee by HPLC analysis; [α]$_D^{23}$=96.8° (c=1.0, CH$_2$Cl$_2$); mp 72–73° C.; IR (thin film) 3061, 2934, 1701 cm$^{-1}$; $^1$H NMR (400 MHz, CDCl$_3$) δ 8.06 (s, 1H), 7.90 (m, 3H), 7.59 (m, 2H), 7.37 (m, 1H) 6.85 (s, 1H), 5.69 (m, 1H), 5.17 (d, J=10.4 Hz, 1H), 5.12 (d, J=17.2 Hz, 1H), 4.20 (dd, J=4.9, 17.0 Hz, 1H), 3.50 (dd, J=6.5, 17.0 Hz, 1H); $^{13}$C NMR {$^1$H} (100 MHz, CDCl$_3$) δ 157.9 (q, J=38 Hz), 133.6, 132.9, 131.2, 129.8, 128.3, 128.1, 127.9, 127.7, 127.4, 124.2, 120.4, 117.6 (q, J=287 Hz), 115.4, 114.7, 50.0, 48.6; HRMS m/z (M$^+$) calcd 318.0980, obsd 318.0974.

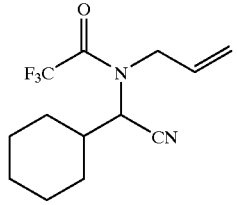

(10h): Product was obtained in 77% yield as a clear oil after purification by flash chromatography (3:2 hexanes:CH$_2$Cl$_2$) and in 57% ee by Chiral GC analysis (γ-TA, 120 ° C. isothermal, t$_r$(major)=15.1 min, t$_r$(minor)=17.4 min); [α]$_D^{23}$=−10.4° (c=1.0, CH$_2$Cl$_2$); IR (thin film) 2936, 2859, 1704 cm$^{-1}$; $^1$H NMR (400 MHz, CDCl$_3$) δ 5.85 (m, 1H), 5.38 (d, J=15.7 Hz, 1H), 5.35 (d, J=9.8 Hz, 1H), 4.65 (d, J=10.6 Hz, 1H), 4.26 (dd, J=4.9, 16.9 Hz, 1H) 4.26 (dd, J=6.9, 16.9 Hz, 1H), 2.09 (m, 2H), 1.84–1.60 (m, 4H), 1.40–0.85 (m, 5H); $^{13}$C NMR {$^1$H} (100 MHz, CDCl$_3$) δ 157.8 (J=37 Hz), 131.6, 120.6, 117.4 (q, J=286 Hz), 115.9, 53.6, 50.4, 38.3, 30.0, 28.9, 25.7, 25.3, 25.1; HRMS m/z (M+NH$_4^+$) calcd 292.1637, obsd 292.1625.

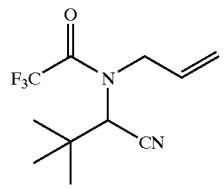

(10i): Product was obtained in 69% yield as a clear oil after purification by flash chromatography (3:2 hexanes:CH$_2$Cl$_2$) and in 37% ee by Chiral GC analysis (γ-TA, 112° C. isothermal, t$_r$(major)=4.4 min, t$_r$(minor)=6.4 min); [α]$_D^{23}$=−20.4° (c=1.0, CH$_2$Cl$_2$); IR (thin film) 2972, 1705 cm$^{-1}$; $^1$H NMR (400 MHz, CDCl$_3$) δ 5.87 (m, 1H), 5.33 (d, J=10.4 Hz, 1H), 5.25 (d, J=17.2 Hz, 1H), 4.25 (s(br), 2H), 1.16 (s, 9H); $^{13}$C NMR {$^1$H} (100 MHz, CDCl$_3$) δ 157.5 (J=37 Hz), 132.0, 119.0, 117.4 (q, J=286 Hz), 115.3, 56.7, 40.5, 38.1, 26.9; HRMS m/z (M+NH$_4^+$) calcd 266.1480, obsd 266.1481.

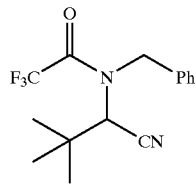

(14): Product was obtained in 88% yield as a white solid after purification by flash chromatography (3:2 hexanes:CH$_2$Cl$_2$) and in 49% ee by Chiral GC analysis (γ-TA, 120° C. isothermal, t$_r$(major)=26.4 min, t$_r$(minor)=28.4 min). Recrystallization from 1:10 EtOAc:hexanes yielded racemic crystals and the from the mother liquor 48% (from imine) of 97.5% ee by Chiral GC analysis; [α]$_D^{23}$=−56.2° (c=1.0, CH$_2$Cl$_2$); mp 95–96° C.; IR (thin film) 2975, 2946, 1691 cm$^{-1}$; $^1$H NMR (400 MHz, CDCl$_3$) δ 7.39 (m, 3H), 7.19 (m, 2H), 4.97 (d, J=16.7 Hz, 1H), 4.72 (d, J=16.7 Hz, 1H), 1.14 (s, 9H); $^{13}$C NMR {$^1$H} (100 MHz, CDCl$_3$) δ 157.4 (J=37 Hz), 134.7, 129.1, 128.5, 126.3, 117.5 (q, J=287 Hz), 115.0, 57.6, 52.4, 38.6, 27.3; HRMS m/z (M$^+$) calcd 298.1293, obsd 298.1297.

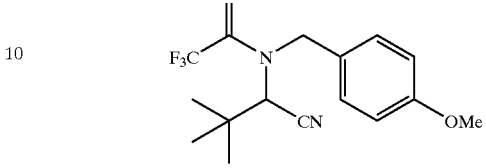

(15): Product was obtained in 67% yield as a white solid after purification by flash chromatography (3:2 hexanes:CH$_2$Cl$_2$) and in 43% ee by Chiral GC analysis (γ-TA, 132° C. isothermal, t$_r$(major)=57.9 min, t$_r$(minor)= 61.3 min); [α]$_D^{23}$=−28.7° (c=1.0, CH$_2$Cl$_2$); 108–109° C.; IR (thin film) 3014, 2976, 2942, 1696, 1518 cm$^{-1}$; $^1$H NMR (400 MHz, CDCl$_3$) δ 7.12 (d, J=8.3 Hz, 2H), 6.91 (d, J=8.3 Hz, 2H), 4.92 (d, J=16.3 Hz, 1H), 4.65 (d, J=16.3 Hz, 1H), 3.80 (s, 3H), 1.13 (s, 9H); $^{13}$C NMR {$^1$H} (100 MHz, CDCl$_3$) δ 159.8, 157.3 (J=37 Hz), 127.9, 126.3, 117.6 (q, J=287 Hz), 115.0, 114.6, 57.4, 55.3, 52.1, 38.5, 27.3; HRMS m/z (M+Na)$^+$ calcd 351.1296, obsd 351.1301.

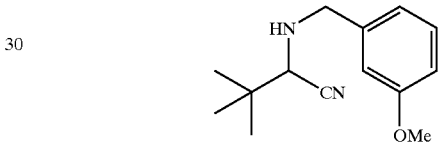

(16): Product was obtained in 74% yield as a white solid after purification by flash chromatography (3:1 hexanes:CH$_2$Cl$_2$) and in 40% ee by Chiral HPLC analysis (as the trifluoroamide) (Chiralcel AS, 0.05% to 1% IPA/Hexanes, 25 min, 1 ml./min, t$_r$(major)=20.9 min, t$_r$(minor)= 16.7 min); [α]$_D^{23}$=54.20 (c=1.0, CH$_2$Cl$_2$); IR (KBr) 3399, 2968, 2940, 2911, 2230, 1602, 1511 cm$^{-1}$; $^1$H NMR (400 MHz, CDCl$_3$) δ 6.92 (m, 1H), 6.83 (m, 2H), 6.72 (m, 1H), 4.47 (d, J=10.1 Hz, 1H), 3.96 (d, J=10.1 Hz, 1H), 3.87 (s, 3H), 1.21 (s, 9H); $^{13}$C NMR {$^1$H} (100 MHz, CDCl$_3$) δ 147.5, 135.4, 121.3, 119.1, 119.0, 111.4, 110.1, 56.2, 55.7, 34.8, 26.2; HRMS m/z (M$^+$) calcd 218.1419, obsd 218.1417.

Synthesis of 18:

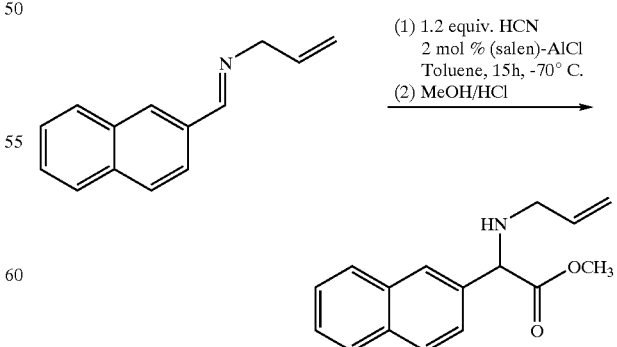

(17): To a flamed dried 100 ml round bottom flask, 1.17 g of 9h (6.00 mmol), 73 mg 8 (0.12 mmol, 2 mol %), and 20 ml of freshly distilled toluene were combined and stirred until homogeneous. The reaction was cooled to −78° C. and 8.5 ml of a solution of HCN in toluene (0.85 M, 7.2 mmol, 1.2 equiv) was added by syringe addition. The mixture was allowed to stir at −70° C. for 15h followed by addition of anhydrous methanolic HCl (3 ml). The solvents were removed in-vacuo and the resulting residue was dissolved in 25 ml of MeOH. The mixture was cooled to 0° C. and HCl gas was bubbled through until the reaction was saturated. The solution was heated to reflux for 6 h, cooled and $H_2O$ was added (3ml). The solvents were removed in-vacuo and the resulting residue was disolved in 50 ml of $H_2O$ and washed with hexanes (3×30 ml). The aqueous layer was made alkaline by addition of saturated $Na_2CO_3$ and extracted with $CH_2Cl_2$ (5×50 ml). The organic extracts were dried over $Na_2SO_4$ and the solvent was removed in-vacuo to yield 1.191 g (78%) of a clear oil.; IR (thin film) 1737 $cm^{-1}$; $^1$H NMR (400 MHz, $CDCl_3$) δ 7.82 (m, 4H), 7.49 (m, 3H), 5.91 (ddt, J=17.2, 10.1, 7.1 Hz, 1H), 5.21 (d, J=17.2 Hz, 1H), 5.13 (d, J=10.1 Hz, 1H), 4.59 (s, 1H), 3.70 (s, 3H), 3.24 (d, J=7.1 Hz, 2H), 2.11 (s(br), 1H); $^{13}$C NMR {$^1$H} (100 MHz, $CDCl_3$) δ 173.4, 136.0, 135.4, 133.3, 133.1, 128.5, 128.0, 127.7, 126.7, 126.2, 126.1, 125.1, 116.7, 64.5, 52.3, 50.0; HRMS m/z (M$^+$) calcd 256.1338, obsd 256.1335.

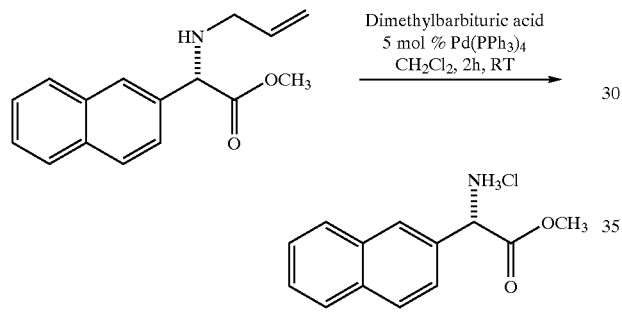

(18): A solution of the allyl protected amino ester 17 (1.191 g, 4.67 mmol) in 12 ml of degassed $CH_2Cl_2$ was added to a schlenk flask containing 1.09 g of dimethylbarbataric acid (7.00 mmol, 1.5 equiv) and 270 mg of $Pd(PPh_3)_4$ (0.23 mmol, 5 mol %). The reaction was allowed to stir for 2 hr followed by in-vacuo removal of solvent. The resulting mixture was dissolved in 50 ml of diethyl ether and washed with saturated $Na_2CO_3$ (3×50 ml) and $H_2O$ (2×50 ml). The organic layer was then extracted with 4N HCl (4×50 ml) and the resulting aqueous layer was washed with ethyl acetate (2×50 ml). The aqueous layer was then filtered to remove palladium salts and the resulting solids were washed with methanol. The aqueous layer and methanol washes were combined and the solvents removed in-vacuo. The resulting white powder was dried under high vacuum to yield 1.109 g (94%) of the amine hydrochloride salt. Recrystallization from MeOH:Et$_2$O (4:1) yielded product in 60% and 99% ee by Chiral HPLC analysis as the trifluoroamide (Chiralcel AS, 5% IPA/Hexanes), 1 ml./min, $t_r$(minor)=8.4 min, $t_r$(major)=10.1 min); $[α]_D^{23}$=134.9° (c=1.0, MeOH); IR (KBr) 2973, 2846, 1740 $cm^{-1}$; $^1$H NMR (400 MHz, DMSO-$d_6$) δ 9.29 (s (broad), 3H)7.93 (m, 4H), 7.59 (m, 3H), 5.43 (s, 1H), 3.70 (s, 3H); $^{13}$C NMR {$^1$H} (100 MHz, DMSO-$d_6$) δ 168.8, 133.0, 132.4, 130.0, 128.7, 128.0, 127.9, 127.7, 127.1, 126.9, 125.1, 55.5, 53.1; HRMS m/z (M$^+$) calcd 215.0946, obsd 215.0941.

Example 2

Preparation of (R,R)-1,2-Diphenyl-1,2-bis(3-tert-butylsalicylideamino)ethane

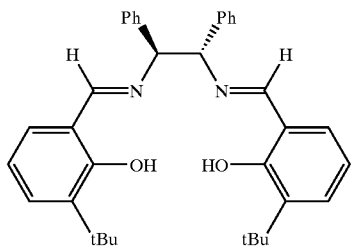

A solution of 360.5 mg (2.0 mmol) of 3-tert-butylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Recrystallization from MeOH/$H_2O$ gave 485.8 mg (91%) of yellow powder, mp 73–74° C. $^1$H NMR ($CDCl_3$) δ 1.42 (s, 18H, $CH_3$), 4.72 (s, 2H, CHN=C), 6.67–7.27 (m, 16H, ArH), 8.35 (s, 2H, CH=N), 13.79 (s, 2H, ArOH) ppm; $^{13}$C NMR ($CDCl_3$) δ 29.3, 34.8, 80.1, 117.8, 118.5, 127.5, 128.0, 128.3, 129.6, 130.1, 137.1, 139.5, 160.2, 166.8 ppm. Anal. Calcd. for $C_{36}H_{40}N_2O_2$. C, 81.17; H, 7.57; N, 5.26. Found: C, 81.17; H, 7.60; N, 5.25.

Example 3

Preparation of (R,R)-1,2-Diphenyl-1,2-bis(3-diphenylmethylsilylsalicylideamino)ethane.

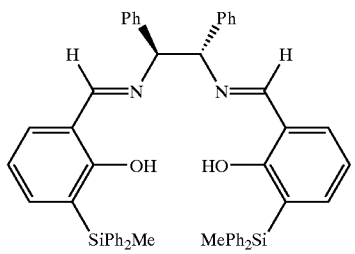

3-(Diphenylmethylsilyl)salicylaldehyde was prepared from 2-bromophenol in 5 steps according to established procedures. A solution of 348.3 mg (1.09 mmol) of 3-(diphenylmethylsilyl)salicylaldehyde and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR ($CDCl_3$) δ 0.95 (s, 3H), 4.68 (s, 2H), 6.72–7.55 (m, 36 H, ArH), 8.37 (s, 2H), 13.34 (s, 2H) ppm.

Example 4

Preparation of 2,2'-Bis(3-tert-Butylsalicylideamino)-1,1'-Binaphthyl

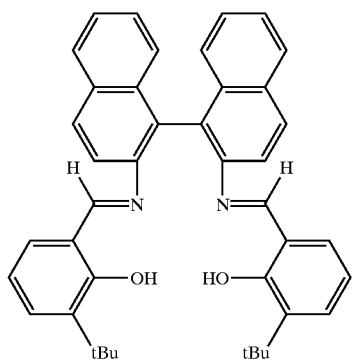

A solution of 725 mg (4.0 mmol) of 3-tert-butylsalicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and then volatile materials were removed under vacuum. The residue was purified by flash chromatography on 80 g $SiO_2$, using 20% $CH_2Cl_2$ in hexane as eluent. The mobile yellow fraction was collected and solvents were removed under vacuum to give 725 mg (1.20 mmol, 59% yield) of the diimine as a yellow powder.

Example 5

Preparation of (S,S)-1,2,-bis(3,5-di-tert-butylsalicylide-amino)cyclohexane (2)

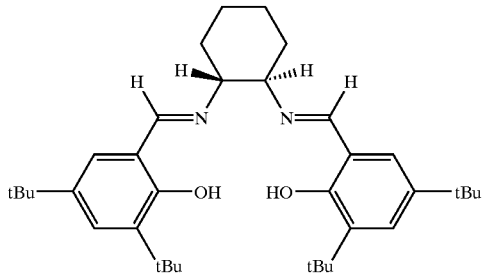

3,5-Di-t-butylsalicylaldehyde (2.0 equivalents) (prepared from the inexpensive, commercially available 2,4-di-t-butylphenol according to Larrow, J. F.; Jacobsen, E. N.; Gao, Y.; Hong, Y.; Nie, X.; Zepp, C. M. *J Org Chem* 1994, 59, 1939) was added as a solid to a 0.2 M solution of (S,S)-1,2-diaminocyclohexane (1.0 equivalent) (Aldrich Chemical Co., Milwaukee, Wis.) in absolute ethanol. The mixture was heated to reflux for 1 hr. and then $H_2O$ was added dropwise to the cooled bright yellow solution. The resulting yellow crystalline solid was collected by filtration and washed with a small portion of 95% ethanol. The yield of analytically pure salen ligand 2 obtained in this manner was 90–97%.

Spectroscopic and analytical data for the salen ligand: $^1H$ NMR ($CDCl_3$) δ 13.72 (s, 1H), 8.30 (S, 1H), 7.30 (d, J=2.3 Hz, 1H), 6.98 (d, J =2.3 Hz, 1H), 3.32 (m, 1H), 20–1.8 (m, 2H), 1.8–1.65 (m, 1H), 1.45 (m, 1H), 1.41 (s, 9H), 1.24 (s, 9H). $^{13}C$ NMR ($CDCl_3$): δ 165.8, 158.0, 139.8, 136.3, 126.0, 117.8, 72.4, 34.9, 33.0, 31.4, 29.4, 24.3. Anal. Calcd. for $C_{36}H_{54}N_2O_2$: C, 79.07; H, 9.95; N, 5.12. Found: C, 79.12; H, 9.97; N, 5.12.

Example 6

Synthesis of a Chiral Porphyrin Ligand

Pyrrole (1.0 equivalents) and salicylaldehyde (1.2 equivalents) are dissolved in propionic acid (1 liter/20ml pyrrole) and the solution is refluxed for 30 minutes. The reaction mixture is allowed to cool to room temperature and stand for one day. The mixture is filtered and the product is recrystallized to yield 5,10,15,20-tetrakis(2'-hydroxyphenyl) porphyrin.

The above-named porphyrin is dissolved in dimethylformamide, cooled to 0° C., and treated with sodium hydride (4 equivalents). The mixture is stirred for 30 minutes, and then a solution of D-threitol 1,4-ditosylate (Aldrich Chemical Co.) in DMF is added slowly. When the addition is finished, the reaction mixture is stirred for 30 minutes more, then carefully quenched. The organic phase is washed with brine and the solvent is evaporated. The residue is purified by HPLC to yield the chiral porphyrin.

Example 7

Enantioselective 1,4-Addition of Azide to N-Ethylmaleimide

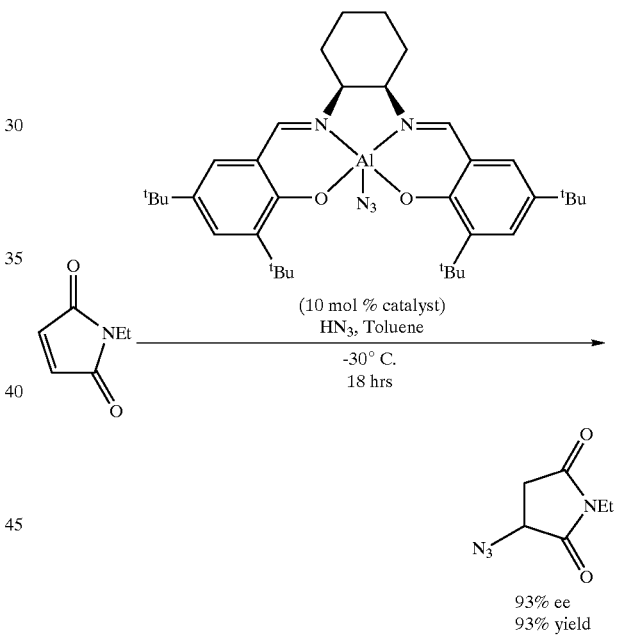

A solution in toluene of N-ethylmaleimide, $HN_3$ (excess relative to the maleimide), and the (salen)$AlN_3$ catalyst depicted above (10 mol % relative to the maleimide) was maintained at −30° C. for 18 h. After a standard quench and work-up of the reaction mixture, the crude material was purified to yield 2-azido-N-ethylsuccinimide (93%, 93% ee).

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A process of stereoselective chemical synthesis which comprises reacting a π-bond-containing substrate represented by the general formula 1 and a nucleophile represented by NuY in the presence of a chiral, non-racemic catalyst to produce a stereoisomerically-enriched addition product 2, wherein said chiral, non-racemic catalyst comprises an asymmetric tetradentate ligand complexed with a main-group metal atom from Group 2, 12, 13, or 14; said catalyst having a rectangular planar or rectangular pyramidal geometry, and said process is represented by:

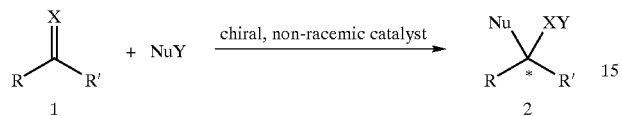

wherein

R, R', and R" represent, independently for each occurrence, hydrogen, alkyl, alkenyl, alkynyl, thioacyl, alkylthio, imine, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, —C(O)$R_{10}$, —C(O)O$R_{10}$, C(O)S$R_{10}$, —OC(O)$R_{10}$, —SC(O)$R_{10}$, —C(O)N($R_{11}$)$_2$, —N($R_{12}$)C(O)N($R_{12}$)$_2$, —N($R_{12}$)C(S)N($R_{12}$)$_2$, or —(CH$_2$)$_m$—$R_{80}$;

$R_{10}$ represents independently for each occurrence H, alkyl, alkenyl, or —(CH$_2$)$_m R_{80}$;

$R_{11}$ represents independently for each occurrence H, alkyl, alkenyl, —(CH$_2$)$_m R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

$R_{12}$ represents independently for each occurrence H, alkyl, or aralkyl;

X is selected from the group consisting of C(R)$_2$, O, S, Se, and NR";

Y is selected, independently for each occurrence, from the group consisting of H, Li, Na, K, Ma, Ca, B, Al, Cu, Ag, Ti, Zr, Si(R)$_3$ and Sn(R)$_3$, and Nu is selected from the group consisting of conjugate bases of weak Bronsted acids and carbanions;

$R_{80}$ represents independently for each occurrence an unsubstituted or substituted aryl, cycloalkyl, cycloalkenyl, heterocycle, or polycycle;

m represents independently for each occurrence an integer in the range 0 to 8 inclusive; and said chiral, non-racemic catalyst is represented by general formula 100;

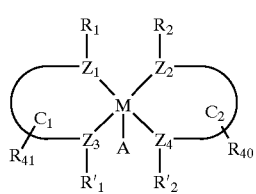

wherein $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached;

$R_{40}$ and $R_{41}$ each independently are absent, or represent one or more covalent substitutions of $C_1$ and $C_2$ with an organic or inorganic substituent permitted by valence requirements of the ring atom to which it is attached;

or any two or more of $R_1$, $R_2$, $R'_1$, $R'_2$, $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as tetradentate;

M represents a main-group metal atom from Group 2, 12, 13 or 14;

A represents a counterion or a nucleophile; and each of $R_1$, $R_2$, $R'_1$, $R'_2$, $R_{40}$, and $R_{41}$ are selected to provide at least one stereogenic center in said tetradentate ligand.

2. The process of claim 1, wherein the metal atom is selected from groups 12, 13, or 14.

3. The process of claim 1, wherein the metal atom is selected from the group consisting of Be, Mg, Ca, Sr, Ba, Zn, Cd, Hg, Al, Ga, In, and Sn.

4. The process of claim 1, wherein the tetradentate ligand is selected from the group consisting of a chiral, non-racemic ligand represented by formula 102:

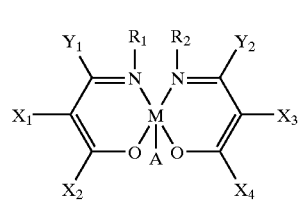

wherein $R_1$, $R_2$, $Y_1$, $Y_2$, $X_1$, $X_2$, $X_3$ and $X_4$ each, independently, represent hydrogen, halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —C(O)$R_{10}$, —C(O)O$R_{10}$, —C(O)S$R_{10}$, —OC(Q)$R_{10}$, —SC(O)$R_{10}$, —C(O)N($R_{11}$)$_2$, or —(CH$_2$)$_m$—$R_7$; or any two or more of $R_1$, $R_2$, $Y_1$, $Y_2$, $X_1$, $X_2$, $X_3$ or $X_4$ taken together form a carbocycle or heterocycle having from 4 to 8 atoms in the ring structure; with the proviso that at least one of $R_1$, $Y_1$, $X_1$ and $X_2$ is covalently bonded to at least one of $R_2$, $Y_2$, $X_3$ and $X_4$ to provide the β-iminocarbonyl as a tetradentate ligand;

$R_7$ represents aryl, cycloalkyl, cycloalkenyl, heterocycle, or polycycle;

$R_{10}$ represents independently for each occurrence H, alkyl, alkenyl, or —(CH$_2$)$_m R_{80}$;

$R_{11}$ represents independently for each occurrence H, alkyl, alkenyl, —(CH$_2$)$_m R_{80}$, —C(O)alkyl, —C(O)

alkenyl, —C(O)alkynyl, or —C(O)(CH$_2$)$_m$R$_{80}$; or two instances of R$_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14;

A represents a counterion or a nucleophile; and each of R$_1$, R$_2$, Y$_1$, Y$_2$, X$_1$, X$_2$, X$_3$ and X$_4$, are selected such that the catalyst is asymmetric;

a chiral, non-racemic ligand represented by the formula 104:

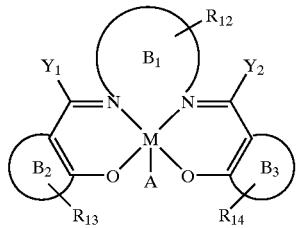

104 wherein

B$_1$ represents alkyl, alkenyl, alkynyl, or —R$_{15}$—R$_{16}$—R$_{17}$—; wherein R$_{15}$ and R$_{17}$ each independently are absent or represent alkyl, alkenyl, or alkynyl; and R$_{16}$ is absent or represents amine, imine, phosphonate, phosphine, silyl, oxygen, sulfur, sulfonyl, selenium, —C(O)—, —C(O)O—, —C(O)S—, —OC(O)—, —SC(O)—, —C(O)N(R$_{11}$)—, or —N(R$_{11}$)C(O)—;

B$_2$ and B$_3$ represent independently for each occurrence a ring selected from the group consisting of cycloalkyl, cycloalkenyl, aryl, and heterocycle; wherein said ring has 4 to 8 atoms;

R$_{12}$, R$_{13}$ and R$_{14}$ each independently are absent, or represent one or more covalent substitutions of B$_1$, B$_2$ and B$_3$ with a halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$; wherein R$_{12}$ occurs on one or more positions of —R$_{15}$—R$_{16}$—R$_{17}$—;

R$_7$ represents aryl, cycloalkyl, cycloalkenyl, heterocycle, or polycycle;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

m represents independently for each occurrence zero or an integer in the range of 1 to 8;

any two or more of the R$_{12}$, R$_{13}$, R$_{14}$, Y$_1$ and Y$_2$ substituted taken together can form a bridging substituent to bridge the two β-iminocarbonyls or bridge different portions of the same β-iminocarbonyl;

M represents a main-group metal atom from Group 2, 12, 13, or 14;

A represents a counterion or a nucleophile; and

B$_2$ and B$_3$ are selected so that the ligand is chiral; or the substituents on B$_1$ are selected so that the ligand is chiral;

a chiral, non-racemic ligand represented by the formula 106:

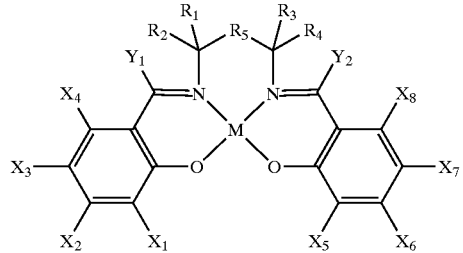

106 wherein

R$_1$, R$_2$, R$_3$, R$_4$, R$_5$, Y$_1$, Y$_2$, X$_1$, X$_2$, X$_3$, X$_4$, X$_5$, X$_6$, X$_7$, and X$_8$ represent independently for each occurrence hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$; or any two or more of the substituents taken together form a carbocyle or heterocycle having at least 4 atoms in the ring structure;

R$_7$ represents aryl, cycloalkyl, cycloalkenyl, heterocycle or polycycle;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14;

provided that if R$_5$ is absent, at least one of R$_1$ and R$_2$ is covalently bonded to at least one of R$_3$ and R$_4$; and the substituents of the salenate ligand are selected such that the salenate has at least one stereogenic center;

a chiral, non-racemic ligand represented by the formula 108;

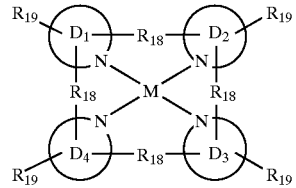

108 wherein

D$_1$, D$_2$, D$_3$ and D$_4$ each represent a heterocycle;

R$_{18}$ is represents independently alkyl, alkenyl, alkynyl, or —R$_{15}$—R$_{16}$—R$_{17}$—; wherein R$_{18}$ contains at least one stereogenic center;

R$_{15}$ and R$_{17}$ each independently are absent or represent alkyl, alkenyl, or alkynyl;

R$_{16}$ is absent or represents an amine, imine, phosphonate, phosphine, silyl, oxygen, sulfonyl, sulfer, selenium, —C(O)—, —C(O)O—, —OC(O)—, —C(O)S—, —SC(O)—, —C(O)N(R$_{11}$)—, or —N(R$_{11}$)C(O)—;

$R_{19}$ is independently absent or represents halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —OC(O)$R_{10}$, —SC(O)$R_{10}$, —C(O)N($R_{11}$)$_2$, or —(CH$_2$)$_m$—$R_7$;

any two or more of $R_{18}$ and $R_{19}$ are covalently linked to form a bridge substitution;

$R_7$ represents aryl, cycloalkyl, cycloalkenyl, heterocycle, or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14; and each $R_{18}$ and $R_{19}$ are selected such that the catalyst is asymmetric;

a chiral, non-racemic ligand represented by the formula 110:

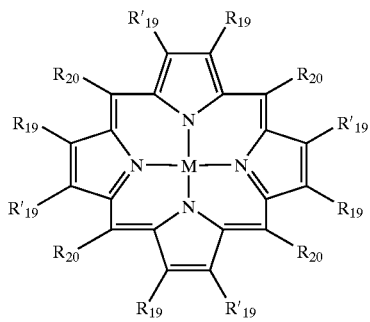

110 wherein $R_{20}$ represents independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoethers, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

$R_{19}$ and $R'_{19}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$; or any two instances of $R_{19}$ and $R'_{19}$ on the same pyrrole can be taken together to form a fused carbocycle or fused heterocycle having from 4 to 7 atoms in the ring structure;

any two or more instances of $R_{19}$, $R'_{19}$ and $R_{20}$ may be covalently cross-linked to form a bridging substituent;

$R_7$ represents aryl, cycloalkyl, cycloalkenyl, heterocycle or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14; and $R_{19}$, $R'_{19}$ and $R_{20}$ are selected such that the catalyst is asymmetric;

a chiral, non-racemic ligand represented by the formula 112:

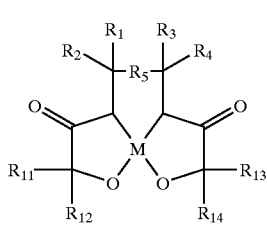

112 wherein $R_1$, $R_2$, $R_3$, $R_4$, $R_5$, $R_{11}$, $R_{12}$, $R_{13}$ and $R_{14}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{60}$, —C(O)O$R_{60}$, —C(O)S$R_{60}$, —OC(O)$R_{60}$, —SC(O)$R_{60}$, —C(O)N($R_{61}$)$_2$, or —(CH$_2$)$_m$—$R_7$; or any two or more instances $R_1$, $R_2$, $R_3$, $R_4$, $R_5$, $R_{11}$, $R_{12}$, $R_{13}$ and $R_{14}$ taken together form a carbocycle or heterocycle having at least 4 atoms in the ring structure;

$R_7$ represents aryl, cycloalkyl, cycloalkenyl, heterocycle or polycycle;

$R_{60}$ represents independently for each occurrence H, alkyl, alkenyl, or —(CH$_2$)$_m$$R_{80}$;

$R_{61}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{61}$ are taken together with the N atom to which they are attached to form a heterocycle having from 4 to 8 atoms;

m is zero or an integer in the range of 1 to 8; and

M represents a main-group metal atom from Group 2, 12, 13, or 14;

provided that if $R_5$ is absent, at least one of $R_1$ and $R_2$ is covalently bonded to at least one of $R_3$ and $R_4$; and the substituents are selected such that the catalyst is asymmetric;

a chiral, non-racemic ligand represented by the formula 114 that is complexed to said metal atom:

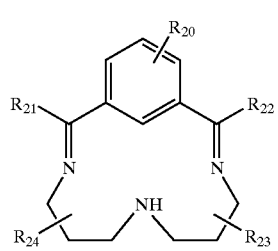

114 wherein $R_{21}$ and $R_{22}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

$R_{20}$ is absent or represents one or more substituents of the pyridine to which it is attached, each substituent independently selected from the group consisting of halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

$R_{23}$ and $R_{24}$ each independently are absent or represent one or more substituents of the 1,3-diiminopropyl to which they are attached, each substituent independently selected from the group consisting of halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$$R_7$;

or any two or more of the $R_{20}$, $R_{21}$, $R_{22}$, $R_{23}$ and $R_{24}$ substituents are covalently linked to form a bridging substituent;

$R_7$ represents aryl, cycloalkyl, cycloalkenyl, heterocycle or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8; and $R_{20}$, $R_{21}$, $R_{22}$, $R_{23}$ and $R_{24}$ are selected such that the catalyst is asymmetric;

a chiral, non-racemic ligand represented by the formula 116 that is complexed to said metal atom:

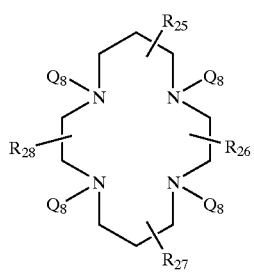

116 wherein $Q_8$ are each independently absent, hydrogen, or lower alkyl;

$R_{25}$, $R_{26}$, $R_{27}$ and $R_{28}$, each independently, represent one or more substituents on the ethyl or propyl diimine to which they are attached, which substituents are selected from the group of hydrogen, halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, and (CH$_2$)$_m$—$R_7$; two or more of the substituents taken together form a bridging substituent;

$R_7$ represents independently for each occurrence aryl, cycloalkyl, cycloalkenyl, heterocycle, or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8; and $Q_8$, $R_{25}$, $R_{26}$, $R_{27}$, and $R_{28}$ are selected such that the catalyst is asymmetric;

and chiral, non-racemic crown ethers.

5. The process of claim 1, wherein the tetradentate ligand has at least one Schiff base which complexes with the main-group metal atom.

6. The process of claim 1, wherein the chiral catalyst has a molecular weight of less than 5,000 a.m.u.

7. The process of claim 1, wherein R and R' in 1 taken together form a carbocyclic or heterocyclic ring having from 4 to 8 atoms in the ring structure.

8. The process of claim 1, wherein R, and R' are chosen such that 1 does not have an internal plane of symmetry.

9. The process of claim 1, wherein the π-bond-containing substrate is selected from the group consisting of an aldehyde, conjugated enal, thioaldehyde, conjugated thioenal, selenoaldehyde, conjugated selenoenal, ketone, conjugated enone, thioketone, conjugated thionone, selenoketone, conjugated selenoenone, imine, oxime, hydrazone, glyoxylate, pyruvate, conjugated enoate, α,β-unsaturated amide, α,β-unsaturated imide, lactone, thionolactone, thiolactone, dithiolactone, lactam, and thiolactam.

10. The process of claim 1, wherein the catalyst is immobilized on an insoluble matrix.

11. The process of claim 1, which process is an enantioselective reaction.

12. The process of claim 1, which process is a diastereoselective reaction.

13. The process of claim 12, which diastereoselective reaction is a kinetic resolution.

14. A stereoselective nucleophilic addition process which comprises:

combining a chiral or prochiral π-bond-containing substrate represented by general formula 1 and a nucleophile represented by NuY in the presence of a chiral, non-racemic catalyst to produce a stereoisomerically enriched product 2, wherein said chiral, non-racemic catalyst comprises a chiral tetradentate ligand having at least one Schiff base nitrogen complexed with a main-group metal atom from group 2, 12, 13, or 14; maintaining the combination under conditions appropriate for said chiral, non-racemic catalyst to catalyze a stereoselective nucleophilic addition reaction between said chiral or prochiral π-bond-containing substrate and said nucleophile, and said process is represented by:

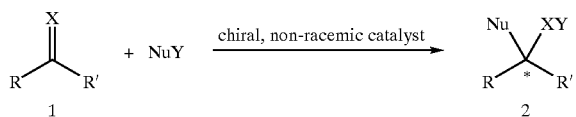

wherein
- R, R', and R" represent, independently for each occurrence, hydrogen, alkyl, alkenyl, alkynyl, thioacyl, alkylthio, imine, amide, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, $-C(O)R_{10}$, $-C(O)OR_{10}$, $-C(O)SR_{10}$, $-OC(O)R_{10}$, $-SC(O)R_{10}$, $-C(O)N(R_{11})_2$, $-N(R_{12})C(O)N(R_{12})_2$, $-N(R_{12})C(S)N(R_{12})_2$, or $-(CH_2)_m-R_{80}$;
- $R_{10}$ represents independently for each occurrence H, alkyl, alkenyl, or $-(CH_2)_m R_{80}$;
- $R_{11}$ represents independently for each occurrence H, alkyl, alkenyl, $-(CH_2)_m-R_{80}$, $-C(O)$alkyl, $-C(O)$alkenyl, $-C(O)$alkynyl, or $-C(O)(CH_2)_m-R_{80}$; or two instances of $R_{11}$ are taken together with the N atom to which they are attached to form a heterocycle having from 4 to 8 atoms;
- $R_{12}$ represents independently for each occurrence H, alkyl, or aralkyl;
- X is selected from the group consisting of $C(R)_2$, O, S, Se, and NR";
- Y is selected, independently for each occurrence, from the group consisting of H, Li, Na, K, Mg, Ca, B, Al, Cu, Ag, Ti, Zr, $Si(R)_3$, and $Sn(R)_3$; and
- Nu is selected from the group consisting of conjugate bases of weak Bronsted acids and carbanions;
- $R_{80}$ represents independently for each occurrence an unsubstituted or substituted aryl, cycloalkyl, cycloalkenyl, heterocycle, or polycycle;
- m represents independently for each occurrence an integer in the range 0 to 8 inclusive; and
- said chiral, non-racemic catalyst is represented by general formula 100:

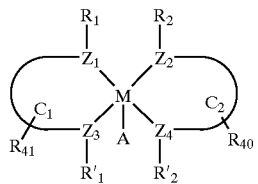

wherein
- $Z_1$, $Z_2$, $Z_3$ and $Z_4$ each represent a Lewis base;
- the $C_1$ moiety, taken with $Z_1$, $Z_3$ and M, and the $C_2$ moiety, taken with $Z_2$, $Z_4$ and M, each, independently, form a heterocycle;
- $R_1$, $R_2$, $R'_1$ and $R'_2$ each, independently, are absent or represent a covalent substitution with an organic or inorganic substituent permitted by valence requirements of the electron donor atom to which it is attached;
- $R_{40}$ and $R_{41}$ each independently are absent, or represent on or more covalent substitutions of $C_1$ and $C_2$ with an organic or inorganic substituent permitted by valence requirements of the ring atom to which it is attached;
- or any two or more of $R_1$, $R_2$, $R'_1$, $R'_2$, $R_{40}$ and $R_{41}$ taken together form a bridging substituent;
- with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as tetradentate;
- M represents a main-group metal atom from Group 2, 12, 13, or 14;
- A represents a counterion or a nucleophile; and
- wherein each of $R_1$, $R_2$, $R'_1$, $R'_2$, $R_{40}$, and $R_{41}$ are selected to provide at least one stereogenic center in said tetradentate ligand.

15. The process of claim 14, wherein the metal is a Group 12, 13, or 14 main-group metal.

16. The process of claim 14, wherein the metal atom is selected from the group consisting of Be, Mg, Ca, Sr, Ba, Zn, Cd, Hg, Al, Ga, In, and Sn.

17. The process of claim 14, wherein the catalyst is represented by the general formula:

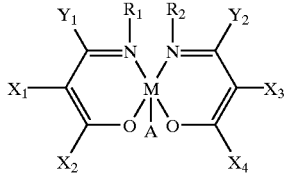

in which
- $R_1$, $R_2$, $Y_1$, $Y_2$, $X_1$, $X_2$, $X_3$ and $X_4$ each, independently, represent hydrogen, halogen, alkyl, alkenyl, alkynyl, hydroxyl, alkoxyl, silyloxy, amino, nitro, thiol, amine, imine, amide, phosphoryl, phosphonate, phosphine, silyl, ether, thioether, sulfonyl, selenoether, $-C(O)R_{10}$, $-C(O)OR_{10}$, $-C(O)SR_{10}$, $-OC(O)R_{10}$, $-SC(O)R_{10}$, or $-(CH_2)_m-R_7$; or any two or more of the substituents taken together form a carbocyle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, an at least one of $Y_1$ and $Y_2$ is a hydrogen;
- $R_7$ represents independently for each occurrence an aryl, cycloalkyl, cycloalkenyl, heterocycle, or polycycle;
- $R_{10}$ represents independently for each occurrence H, alkyl, alkenyl, or $-(CH_2)_m R_7$;
- m represents independently for each occurrence zero or an integer in the range of 1 to 8;
- M represents the main-group metal atom from Group 2, 12, 13, or 14;
- A represents a counterion or a nucleophile; and
- wherein each of of the substituents $R_1$, $R_2$, $Y_1$, $Y_2$, $X_1$, $X_2$, $x_3$ and $X_4$, are selected such that the catalyst is asymmetric.

18. The process of claim 14, wherein R and R' in 1 taken together form a carbocyclic or heterocyclic ring having from 4 to 8 atoms in the ring structure.

19. The process of claim 14, wherein R and R' are chosen such that 1 does not have an internal plane of symmetry.

20. The process of claim 14, wherein the π-bond-containing substrate is selected from the group consisting of aldehyde, conjugated enal, thioaldehyde, conjugated thioenal, selenoaldehyde, conjugated selenoenal, ketone, conjugated enone, thioketone, conjugated thioenone, selenoketone, conjugated selenoenone, imine, oxime, hydrazone, glyoxylate, pyruvate, conjugated enoate, α,β-unsaturated amide, α,β-unsaturated imide, lactone, thionolactone, thiolactone, dithiolactone, lactam, and thiolactam.

21. The process of claim 14, which process is an enantioselective reaction.

22. The process of claim 14, which process is a diastereoselective reaction.

23. The process of claim 22, which diastereoselective reaction produces a kinetic resolution.

24. The process of claim 14, wherein the chiral, non-racemic catalyst has a molecular weight of less than 5,000 a.m.u.

25. A method for catalyzing a stereoselective nucleophilic addition reaction which comprises:

combining a chiral or prochiral π-bond-containing substrate represented by formula 1 and a nucleophile represented by NuY in the presence of a chiral, non-racemic catalyst to produce a stereoisomerically enriched product 2, wherein said chiral catalyst comprises a chiral tetradentate ligand complexed with a main-group metal atom from Group 2, 12, 13, or 14; and maintaining the combination under conditions appropriate for said chiral, non-racemic catalyst to catalyze a stereoselective nucleophilic addition reaction between said π-bond-containing substrate and said nucleophile, and said process is represented by:

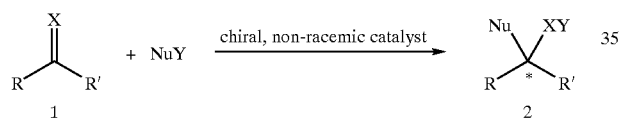

wherein

R, R', and R" represent, independently for each occurrence, hydrogen, alkyl, alkenyl, alkynyl, thioacyl, alkylthio, imine, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, $-C(O)R_{10}$, $-C(O)OR_{10}$, $-C(O)SR_{10}$, $-OC(O)R_{10}$, $-SC(O)R_{10}$, $-C(O)N(R_{11})_2$, $-N(R_{12})C(O)N(R_{12})_2$, $-N(R_{12})C(S)N(R_{12})_2$, or $-(CH_2)_m-R_{80}$;

$R_{10}$ represents independently for each occurrence H, alkyl, alkenyl, or $-(CH_2)_m R_{80}$;

$R_{11}$ represents independently for each occurrence H, alkyl, alkenyl, $-(CH_2)_m-R_{80}$, $-C(O)$alkyl, $-C(O)$alkenyl, $-C(O)$alkynyl, or $-C(O)(CH_2)_m-R_{80}$; or two instances of $R_{11}$ are taken together with the N atom to which they are attached to form a heterocycle having from 4 to 8 atoms;

$R_{12}$ represents independently for each occurrence H, alkyl, or aralkyl;

X is selected from the group consisting of $C(R)_2$, O, S, Se, and NR";

Y is selected, independently for each occurrence, from the group consisting of H, Li, Na, K, Ma, Ca, B, Al, Cu, Ag, Ti, Zr, $Si(R)_3$ and $Sn(R)_3$;

Nu is selected from the group consisting of conjugate bases of weak Bronsted acids and carbanions;

$R_{80}$ represents independently for each occurrence an unsubstituted or substituted aryl, cycloalkyl, cycloalkenyl, heterocycle, or polycycle;

m represents independently for each occurrence an integer in the range 0 to 8 inclusive; and said chiral, non-racemic catalyst is represented by general formula 100:

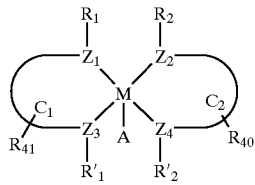

wherein $Z_1$, $Z_2$, $Z_3$ and $Z_4$ each represent a Lewis base;

the $C_1$ moiety, take with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached;

$R_{40}$ and $R_{41}$ each independently are absent, or represent on or more covalent substitutions of $C_1$ and $C_2$ with an organic or inorganic substituent permitted by valence requirements of the ring atom to which it is attached;

or any two or more of $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$ and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as tetradentate;

M represents a main-group metal atom from Group 2, 12, 13, or 14;

A represents a counterion or a nucleophile; and each of $R_1$, $R_2$, $R'_1$, $R'_2$, $R_{40}$ and $R_{41}$ are selected to provide at least one stereogenic center in said tetradentate ligand.

26. The method of claim 25, wherein $R_1$, $R_2$, $R'_1$ and $R'_2$, independently, represent hydrogen, halogen, alkyl, alkenyl, alkynyl, hydroxyl, alkoxyl, silyloxy, amino, nitro, thiol, amine, imine, amide, phosphoryl, phosphonate, phosphine, silyl, ether, thioether, sulfonyl, selenoether, $-C(O)R_{10}$, $-C(O)OR_{10}$, $-C(O)SR_{10}$, $-OC(O)R_{10}$, $-SC(O)R_{10}$, or $-(CH_2)_m-R_7$;

each $R_{40}$ and $R_{41}$ occuring in 100 independently represent hydrogen, halogen, alkyl, alkenyl, alkynyl, hydroxyl, alkoxyl, silyloxy, amino, nitro, thiol, amine, imine, amide, phosphoryl, phosphonate, phosphine, silyl, ether, thioether, sulfonyl, selenoether, $-C(O)R_{10}$, $-C(O)OR_{10}$, $-C(O)SR_{10}$, $-OC(O)R_{10}$, $-SC(O)R_{10}$, or $-(CH_2)_m-R_7$;

$R_7$ represents independently for each occurrence aryl, cycloalkyl, cycloalkenyl, heterocycle, or polycycle;

$R_{10}$ represents independently for each occurrence H, alkyl, alkenyl, or —$(CH_2)_m R_7$; and m represents independently for each occurrence zero or an integer in the range of 1 to 8.

27. The method of claim 25, wherein each $Z_1$, $Z_2$, $Z_3$ and $Z_4$ are independently selected from the group consisting of nitrogen, oxygen, phosphorus, arsenic, and sulfur.

28. The method of claim 25, wherein the metal atom is selected from the group consisting of Be, Mg, Ca, Sr, Ba, Zn, Cd, Hg, Al, Ga, In, and Sn.

29. The method of claim 25, wherein M is a Group 12, 13, or 14 main-group metal.

30. The method of claim 29, wherein M is Al(III).

31. The method of claim 25, wherein the tetradentate ligand is selected from the group consisting of a chiral, non-racemic ligand represented by the formula 102:

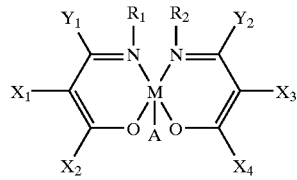

102 wherein $R_1$, $R_2$, $Y_1$, $Y_2$, $X_1$, $X_2$, $X_3$, and $X_4$ each, independently, represent hydrogen, halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —$C(O)R_{10}$, —$C(O)OR_{10}$, —$C(O)SR_{10}$, —$OC(O)R_{10}$, —$SC(O)R_{10}$, —$C(O)N(R_{11})_2$, or —$(CH_2)_m$—$R_7$; or any two or more of $R_1$, $R_2$, $Y_1$, $Y_2$, $X_1$, $X_2$, $X_3$ or $X_4$ taken together form a carbocycle or heterocycle having from 4 to 8 atoms in the ring structure; with the proviso that at least one of $R_1$, $Y_1$, $X_1$ an $X_2$is covalently bonded to at least one of $R_2$, $Y_2$, $X_3$ and $X_4$ to provide th β-iminocarbonyl as a tetradentate ligand;

$R_7$ represents aryl, cycloalkyl, cycloalkenyl, heterocycle, or polycycle;

$R_{10}$ independently for each occurrence H, alkyl, alkenyl, or —$(CH_2)_m R_{80}$;

$R_{11}$ represents independently for each occurrence H, alkyl, alkenyl, —$(CH_2)_m$—$R_{80}$, —$C(O)$alkyl, —$C(O)$alkenyl, —$C(O)$alkynyl, —$C(O)(CH_2)_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14;

A represents a counterion or a nucleophile; and each of $R_1$, $R_2$, $Y_1$, $Y_2$, $X_1$, $X_2$, $X_3$ and $X_4$, are selected such that the catalyst is asymmetric;

a chiral, non-racemic ligand represented by the formula 104:

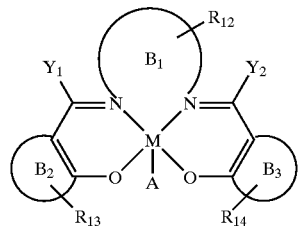

104 wherein $B_1$ represents alkyl, alkenyl, alkynyl, —$R_{15}$—$R_{16}$—$R_{17}$—; or wherein $R_{15}$ and $R_{17}$ each independently are absent or represent alkyl, alkenyl, or alkynyl; and $R_{16}$ is absent or represents amine, imine, phosphonate, phosphine, silyl, oxygen, sulfur, sulfonyl, selenium, —$C(O)$—, —$C(O)O$—, —$C(O)S$—, —$OC(O)$—, —$SC(O)$—, —$C(O)N(R_{11})$—, or —$N(R_{11})C(O)$—;

$B_2$ and $B_3$ represent independently for each occurrence a ring selected from the group consisting of cycloalkyl, cycloalkenyl, aryl, and heterocycle; wherein said ring has 4 to 8 atoms;

$R_{12}$, $R_{13}$ and $R_{14}$ each independently are absent, or represent one or more covalent substitutions of $B_1$, $B_2$ and $B_3$ with a halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —$C(O)R_{10}$, —$C(O)OR_{10}$, —$C(O)SR_{10}$, —$OC(O)R_{10}$, —$SC(O)R_{10}$, —$C(O)N(R_{11})_2$, or —$(CH_2)_m$—$R_7$; wherein $R_{12}$ occurs on one or more positions of —$R_{15}$—$R_{16}$—$R_{17}$—;

$R_7$ represents aryl, cycloalkyl, cycloalkenyl, heterocycle, or polycycle;

$R_{10}$ represents independently for each occurrence H, alkyl, alkenyl, or —$(CH_2)_m R_{80}$;

$R_{11}$ represents independently for each occurrence H, alkyl, alkenyl, —$(CH_2)_m$—$R_{80}$, —$C(O)$alkyl, —$C(O)$alkenyl, —$C(O)$alkynyl, or —$C(O)(CH_2)_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

any two or more of the $R_{12}$, $R_{13}$, $R_{14}$, $Y_1$ and $Y_2$ substituted taken together can form a bridging substituent to bridge the two β-iminocarbonyls or bridge different portions of the same β-iminocarbonyl;

M represents a main-group metal atom from Group 2, 12, 13, or 14;

A represents a counterion or a nucleophile; and $B_2$ and $B_3$ are selected so that the ligand is chiral; or the substituents on $B_1$ are selected so that the ligand is chiral;

a chiral, non-racemic ligand represented by the formula 106:

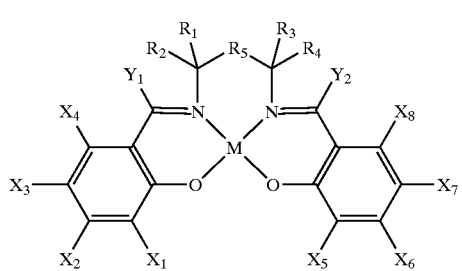

wherein $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$ represent independently for each occurrence hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)$R_{10}$, —C(O)O$R_{10}$, —C(O)S$R_{10}$, —O(O)$R_{10}$, —SC(O)$R_{10}$, —C(O)N($R_{11}$)$_2$, or —(CH$_2$)$_m$—$R_7$; or any two or more of the substituents taken together form a carbocyle or heterocycle having at least 4 atoms in the ring structure;

$R_7$ represents aryl, cycloalkyl, cycloalkenyl, heterocycle or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13, or 14; and provided that if $R_5$ is absent, at least one of $R_1$ and $R_2$ is covalently bonded to at least one of $R_3$ and $R_4$; and the substituents of the salenate ligand are selected such that the salenate has at least one stereogenic center;

a chiral, non-racemic ligand represented by the formula 108:

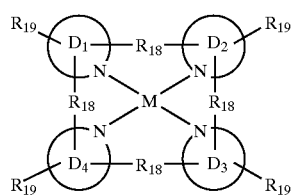

wherein $D_1$, $D_2$, $D_3$ and $D_4$ each represent a heterocycle;

$R_{18}$ represents independently alkyl, alkenyl, alkynyl, or —$R_{15}$—$R_{16}$—$R_{17}$—; wherein $R_{18}$ contains at least one stereogenic center;

$R_{15}$ and $R_{17}$ each independently are absent or represent alkyl, alkenyl, or alkynyl;

$R_{16}$ is absent or represents an amine, imine, phosphonate, phosphine, silyl, oxygen, sulfonyl, sulfer, selenium, —C(O)—, —C(O)O—, —OC(O)—, —C(O)S—, —SC(O)—, —C(O)N($R_{11}$)—, or —N($R_{11}$)C(O)—;

$R_{19}$ is independently absent or represents halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

any two or more of $R_{18}$ and $R_{19}$ are covalently linked to form a bridge substitution;

$R_7$ represents aryl, cycloalkyl, cycloalkenyl, heterocycle, or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13; or 14; and each $R_{18}$ and $R_{19}$ are selected such that the catalyst is asymmetric;

a chiral, non-racemic ligand represented by the formula 110:

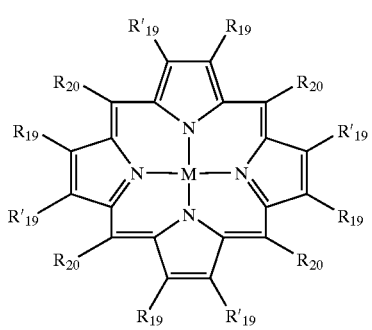

wherein $R_{20}$ represents independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoethers, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

$R_{19}$ and $R'_{19}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$; or any two instances of $R_{19}$ and $R'_{19}$ on the same pyrrole can be taken together to form a fused carbocycle or fused heterocycle having from 4 to 7 atoms in the ring structure;

any two or more instances of $R_{19}$, $R'_{19}$ and $R_{20}$ may be covalently cross-linked to form a bridging substituent;

$R_7$ represents aryl, cycloalkyl, cycloalkenyl, heterocycle or polycycle;

$R_{10}$ represents independently for each occurrence H, alkyl, alkenyl, or —(CH$_2$)$_m$$R_{80}$;

$R_{11}$ represents independently for each occurrence H, alkyl, alkenyl, —(CH$_2$)$_m$—$R_{80}$, —C(O)alkyl, —C(O)

alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

m represents independently for each occurrence zero or an integer in the range of 1 to 8;

M represents a main-group metal atom from Group 2, 12, 13; or 14; and

R$_{19}$, R'$_{19}$ and R$_{20}$ are selected such that the catalyst is asymmetric;

a chiral, non-racemic ligand represented by the formula 112:

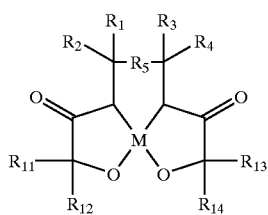

112 wherein

R$_1$, R$_2$, R$_3$, R$_4$, R$_5$, R$_{11}$, R$_{12}$, R$_{13}$ and R$_{14}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)R$_{60}$, —C(O)OR$_{60}$, —C(O)SR$_{60}$, —OC(O)R$_{60}$, —SC(O)R$_{60}$, —C(O)N(R$_{61}$)$_2$, or —(CH$_2$)$_m$—R$_7$; or any two or more instances of R$_1$R$_2$, R$_3$, R$_4$, R$_5$, R$_{11}$, R$_{12}$, R$_{13}$ and R$_{14}$ taken together form a carbocycle or heterocycle having at least 4 atoms in the ring structure;

R$_7$ represents aryl, cycloalkyl, cycloalkenyl, heterocycle or polycycle;

R$_{60}$ represents independently for each occurrence H, alkyl, alkenyl, or —(CH$_2$)$_m$R$_{80}$;

R$_{61}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{61}$ are taken together with the N atom to which they are attached to form a heterocycle having from 4 to 8 atoms;

m is zero or an integer in the range of 1 to 8; and

M represents a main-group metal atom from Group 2, 12, 13, or 14;

provided that if R$_5$ is absent, at least one of R$_1$ and R$_2$ is covalently bonded to at least one of R$_3$ and R$_4$; and the substituents are selected such that the catalyst is asymmetric;

a chiral, non-racemic ligand represented by the formula 114 that is complexed to said metal atom:

114

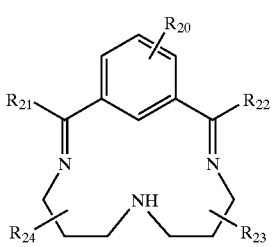

wherein

R$_{21}$ and R$_{22}$ represent independently for each occurrence hydrogen, halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$;

R$_{20}$ is absent or represents one or more substituents of the pyridine to which it is attached, each substituent independently selected from the group consisting of halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$;

R$_{23}$ and R$_{24}$ each independently are absent or represent one or more substituents of the 1,3-diiminopropyl to which they are attached, each substituent independently selected from the group consisting of halogen, alkyl, alkenyl, alkynyl, hydroxyl, alkoxyl, silyloxy, amino, nitro, thiol amine, imine, phosphonate, phosphine, silyl, ether, thioether, sulfonyl, selenoether, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$;

or any two or more of the R$_{20}$, R$_{21}$, R$_{22}$, R$_{23}$ and R$_{24}$ substituents are covalently linked to form a bridging substituent;

R$_7$ represents aryl, cycloalkyl, cycloalkenyl, heterocycle or polycycle;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$R$_{80}$; or two instances of R$_{11}$ are taken together with the N atom to which they are attached to form a heterocycle having from 4 to 8 atoms;

m represents independently for each occurrence zero or an integer in the range of 1 to 8; and R$_{20}$, R$_{21}$, R$_{22}$, R$_{23}$ and R$_{24}$ are selected such that the catalyst is asymmetric;

a chiral, non-racemic ligand represented by the formula 116 that is complexed to said metal atom:

116

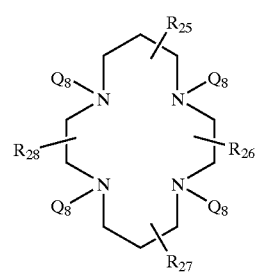

wherein

Q$_8$ are each independently absent, hydrogen, or lower alkyl;

R$_{25}$, R$_{26}$, R$_{27}$ and R$_{28}$, each independently, represent one or more substituents on the ethyl or propyl diimine to which they are attached, which substituents are selected from the group of hydrogen, halogen, alkyl, alkenyl, alkynyl, hydroxyl, alkoxyl, silyloxy, amino, nitro, thiol, amine, imine, phosphonate, phosphine, silyl, ether, thioether, sulfonyl, selenoether, —C(O)R$_{10}$, —C(O)R$_{10}$, —C(O)SR$_{10}$, —OC(O)R$_{10}$, —SC(O)R$_{10}$, —C(O)N(R$_{11}$)$_2$, and —(CH$_2$)$_m$—R$_7$; or any two or more of the substituents taken together form a bridging substituent;

R$_7$ represents independently for each occurrence aryl, cycloalkyl, cycloalkenyl, heterocycle, or polycycle;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

m represents independently for each occurrence zero or an integer in the range of 1 to 8; and Q$_8$, R$_{25}$, R$_{26}$, R$_{27}$, and R$_{28}$ are selected such that the catalyst is asymmetric; and chiral non-racemic crown ethers.

32. The method of claim 25, wherein R and R' in 1 taken together form a carbocyclic or heterocyclic ring having from 4 to 8 atoms in the ring structure.

33. The method of claim 25, wherein R, and R' are chosen such that 1 does not have an internal plane of symmetry.

34. The method of claim 25, wherein the π-bond-containing substrate is selected from the group consisting of aldehydes, conjugated enal, thioaldehyde, conjugated thioenal, selenoaldehyde, conjugated selenoenal, ketone, conjugated enone, thioketone, conjugated thioenone, selenoketone, conjugated selenoenone, imine, oxime, hydrazone, glyoxylate, pyruvate, conjugated enoate, α,⊕-unsaturated amide, α,β-unsaturated imide, lactone, thionolactone, thiolactone, dithiolactone, lactam, and thiolactam.

35. The process of claim 20, which process is an enantioselective reaction.

36. The method process of claim 20, which process is a diastereoselective reaction.

37. The method process of claim 36, which diastereoselective reaction produces a kinetic resolution.

38. A method for synthesis of stereoisomerically enriched chiral compounds, comprising reacting a prochiral or chiral π-bond-containing substrate with a nucleophile in the presence of a chiral, non-racemic catalyst, and under conditions wherein said chiral catalyst catalyzes a stereoselective nucleophile addition reaction between said π-bond-containing substrate and said nucleophile, to produce a product which is stereoisomerically-enriched relative to a racemic mixture produced—in the case of a prochiral π-bond-containing substrate—or to the 1:1 ratio of diastereoisomers produced—in cases wherein the π-bond-containing substrate is chiral—in the absence of said chiral catalyst; wherein the π-bond-containing substrate is represented by the general formula 1, the nucleophile is represented by NuY, and the product of the subject process is represented by 2:

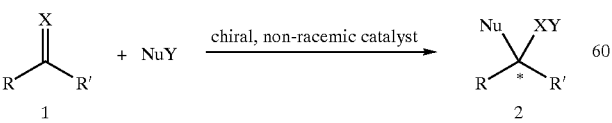

wherein

R, R', and R" represent, independently for each occurrence, hydrogen, alkyl, alkenyl, alkynyl, thioacyl, alkylthio, imine, amide, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, —N(R$_{12}$)C(O)N(R$_{12}$)$_2$, —N(R$_{12}$)C(S)N(R$_{12}$)$_2$, or —(CH$_2$)$_m$—R$_{80}$;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

R$_{12}$ represents independently for each occurrence H, alkyl, or aralkyl;

X is selected from the group consisting of C(R)$_2$, O, S, Se and NR";

Y is selected, independently for each occurrence, from the group consisting of H, Li, Na, K, Mg, Ca, B, Al, Cu, Ag, Ti, Zr, Si(R)$_3$, and Sn(R)$_3$;

Nu is selected from the group consisting of conjugate bases of weak Bronsted acids and carbanions;

R$_{80}$ represents independently for each occurrence an unsubstituted or substituted aryl, a cycloalkyl, a cycloalkenyl, a heterocycle, or a polycycle; and m represents independently for each occurrence an integer in the range 0 to 8 inclusive; and the chiral catalyst is represented by the general formula:

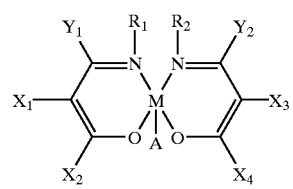

wherein the substituents R$_1$, R$_2$, Y$_1$, Y$_2$, X$_1$, X$_2$, X$_3$ and X$_4$ each, independently, represent hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, ester, —C(O)R$_{10}$, —C(O)OR$_{10}$, —C(O)SR$_{10}$, —OC(O)R$_{10}$, —SC(O)R$_{10}$, —C(O)N(R$_{11}$)$_2$, or —(CH$_2$)$_m$—R$_7$; or any two or more of the substituents taken together form a carbocyle or heterocycle ring having from 4 to 8 atoms in the ring structure, with the proviso that at least one of R$_1$, Y$_1$, X$_1$ and X$_2$ is covalently bonded to at least one of R$_2$, Y$_2$, X$_3$ and X$_4$ to provide the β-iminocarbonyls to which they are attached as a tetradentate ligand, and at least one of Y$_1$ and Y$_2$ is a hydrogen;

R$_7$ represents an aryl, a cycloalkyl, a cycloalkenyl, a heterocycle, or a polycycle;

R$_{10}$ represents independently for each occurrence H, alkyl, alkenyl, or —(CH$_2$)$_m$R$_{80}$;

R$_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of R$_{11}$ are taken together with the N atom to which they are attached to form a heterocycle having from 4 to 8 atoms;

m represents independently for each occurrence zero or an integer in the range of 1 to 8;

M represents the main-group metal atom from Group 2, 12, 13, or 14;

A represents a counterion or a nucleophile; and wherein each of $R_1$, $R_2$, $Y_1$, $Y_2$, $X_1$, $X_2$, $X_3$ and $X_4$, are selected such that the catalyst is asymmetric.

39. The method of claim 38, wherein the metal atom is selected from the group consisting of Be, Mg, Ca, Sr, Ba, Zn, Cd, Hg, Al, Ga, In, and Sn.

40. The method of claim 38, wherein M is a Group 12, 13, or 14 main-group metal.

41. The method of claim 40, wherein M is Al(III).

42. The method of claim 38, wherein the chiral, non-racemic catalyst is represented by the general formula 104:

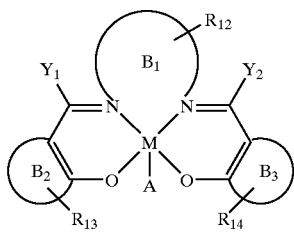

in which the $B_1$ moiety represents a diimine bridging substituent represented by —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents amine, imine, amide, phosphoryl, silyl, oxygen, sulfur, sulfonyl, selenium, —C(O)—$(CH_2)_m$—, —$(CH_2)_m$C(O)—, —C(O)O$(CH_2)_m$—, —$(CH_2)_m$O(O)C—, —C(O)S$(CH_2)_m$—, or —$(CH_2)_m$S(O)C—;

each of $B_2$ and $B_3$ independently represent rings selected from a group consisting of cycloalkyls, cycloakenyls, aryls, and heterocyclic rings, which ring comprising from 4 to 8 atoms in a ring structure;

$Y_1$ and $Y_2$ each independently represent hydrogen, halogen, alkyl, alkenyl, alkynyl, hydroxyl, alkoxyl, silyloxy, amino, nitro, thiol, amine, imine, amide, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, or —$(CH_2)_m$—$R_7$, $R_{12}$, $R_{13}$, and $R_{14}$ each independently are absent, or represent one or more covalent substitutions of $B_1$, $B_2$ and $B_3$ with halogen, alkyl, alkenyl, alkynyl, hydroxyl, alkoxyl, silyloxy, amino, nitro, thiol, amines, imine, amide, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, or —$(CH_2)_m$—$R_7$, wherein $R_{12}$ can occur on one or more positions of —$R_{15}$—$R_{16}$—$R_{17}$—, or any two or more of the $R_{12}$, $R_{13}$, $R_{14}$, $Y_1$ and $Y_2$ taken together form a bridging substituent;

$R_7$ represents independently for each occurrence aryl, cycloalkyl, cycloalkenyl, heterocycle, or polycycle;

$R_{10}$ represents independently for each occurrence H, alkyl, alkenyl, —$(CH_2)_m R_7$;

m represents independently for each occurrence zero or an integer in the range of 1 to 8;

M represents a main-group metal atom from Group 2, 12, 13, or 14;

A represents a counterion or a nucleophile and wherein $R_{12}$, $R_{13}$, $R_{14}$, $Y_1$ and $Y_2$ are selected such that the catalyst is asymmetric.

43. The method of claim 38, wherein R and R' in 1 taken together form a carbocyclic or heterocyclic ring having from 4 to 8 atoms in the ring structure.

44. The method of claim 38, wherein R, and R' are chosen such that 1 does not have an internal plane of symmetry.

45. The method of claim 38, wherein the π-bond-containing substrate is selected from the group consisting of aldehyde, conjugated enal, thioaldehyde, conjugated thioenal, selenoaldehyde, conjugated selenoenal, ketone, conjugated enone, thioketone, conjugated thioenone, selenoketone, conjugated selenoenone, imine, oxime, hydrazone, glyoxylate, pyruvate, conjugated enoate, α,β-unsaturated amide, α,β-unsaturated imide, lactone, thionolactone, thiolactone, dithiolactone, lactam, and thiolactam.

46. The method of claim 38, which process is an enantioselective reaction.

47. The method of claim 38, which process is a diastereoselective reaction.

48. The method of claim 47, which diastereoselective reaction produces a kinetic resolution.

49. A method of realizing a stereoselective addition of a nucleophile to a prochiral or chiral π-bond-containing substrate, wherein the π-bond-containing substrate is represented by the general formula 1, and the nucleophile is represented by NuY, to give a product represented by 2:

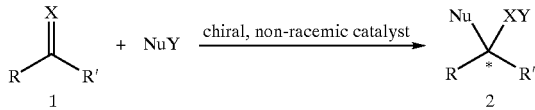

wherein

R, R', and R" represent, independently for each occurrence, hydrogen, alkyl, alkenyl, alkynyl, acyl, thioacyl, alkylthio, imine, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, —C(O)$R_{10}$, —C(O)O$R_{10}$, —C(O)S$R_{10}$, —OC(O)$R_{10}$, —SC(O)$R_{10}$, —C(O)N$(R_{11})_2$, —N$(R_{12})$C(O)N$(R_{12})_2$, —N$(R_{12})$C(S)N$(R_{12})_2$, or —$(CH_2)_m$—$R_{80}$;

$R_{10}$ represents independently for each occurrence H, alkyl, alkenyl, or —$(CH_2)_m R_{80}$;

$R_{11}$ represents independently for each occurrence H, alkyl, alkenyl, —$(CH_2)_m$—$R_{80}$, C(O)alkyl, —C(O)alkenyl, —C(O)alkynyl, or —C(O)$(CH_2)_m$—$R_{80}$; or two instances of $R_{11}$ are taken together with the N atom to which they are attached to form a heterocycle having from 4 to 8 atoms;

$R_{12}$ represents independently for each occurrence H, alkyl, or aralkyl;

X is selected from the group consisting of $C(R)_2$, O, S, Se and NR";

Y is selected, independently for each occurrence, from the group consisting of H, Li, Na, K, Mg, Ca, B, Al, Cu, Ag, Ti, Zr, Si$(R)_3$ and Sn$(R)_3$; and Nu is selected from the group consisting of conjugate bases of weak Bronsted acids and carbanions;

$R_{80}$ represents independently for each occurrence an unsubstituted or substituted aryl, a cycloalkyl, a cycloalkenyl, a heterocycle, or a polycycle;

m represents independently for each occurrence an integer in the range 0 to 8 inclusive; and which method comprises reacting said π-bond-containing substrate with said nucleophile in the presence of at least a catalytic amount of a chiral tetradentate metallosalenate catalyst represented by the general formula 106:

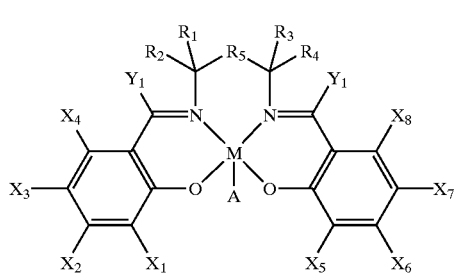

106 wherein each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$;

$R_5$ is hydrogen, alkyl, alkenyl, alkynyl, alkoxyl, silyloxy, amino, thiol, amine, imine, amide, phosphoryl, phosphonate, phosphine, silyl, ether thioether, sulfonyl, selenoether, —C(O)—, —C(O)O—, —C(O)S—, —OC(O)—, or —SC(O)—;

or any two or more of the substituents taken together form a carbocycle or heterocycle having from 4 to 10 atoms in the ring structure;

$R_7$ represents independently for each occurrence aryl, cycloalkyl, cycloalkenyl, heterocycle, or polycycle;

$R_{10}$ represents independently for each occurrence H, alkyl, alkenyl, or —(CH$_2$)$_m R_7$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$, or two instances of $R_{11}$ are taken together with the N atom to which they are attached to form a heterocycle having from 4 to 8 atoms;

m represents independently for each occurrence zero or an integer in the range of 1 to 8;

M represents a main-group metal atom from Groups 2, 12, 13, or 14;

A represents a counterion or a nucleophile; and if $R_5$ is absent, at least one of $R_1$ and $R_2$ is taken together with at least one of $R_3$ and $R_4$ to form a bridging substituent, and each of the substituents of 106 are selected such that the salenate is asymmetric.

50. The method of claim 49, wherein the substituents $R_1$, $R_2$, $R_3$, and $R_4$ each independently represent hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—$R_7$; or any two of the substituents $R_1$, $R_2$, and $R_5$, or $R_3$, and $R_4$ taken together form a carbocylic or heterocyclic ring having from 4 to 8 atoms in the ring structure; and $R_7$ represents an aryl, a cycloalkyl, a cycloalkenyl, a heterocycle or a polycycle; and m is zero or an integer in the range of 1 to 8.

51. The method of claim 49, wherein R, and R' are chosen such that 1 does not have an internal plane of symmetry.

52. The method of claim 49, wherein the π-bond-containing substrate is selected from the group consisting of aldehydes, conjugated enal, thioaldehyde, conjugated thioenal, selenoaldehyde, conjugated selenoenal, ketone, conjugated enone, thioketone, conjugated thioenone, selenoketone, conjugated selenoenone, imine, oxime, hydrazone, glyoxylate, pyruvate, conjugated enoate, α,β-unsaturated amide, α,β-unsaturated imide, lactone, thionolactone, thiolactone, dithiolactone, lactam, and thiolactam.

53. The method of claim 49, wherein the metal atom is selected from the group consisting of Be, Mg, Ca, Sr, Ba, Zn, Cd, Hg, Al, Ga, In, and Sn.

54. The method of claim 49, wherein M is a Group 12, 13, or 14 main-group metal.

55. The method of claim 54, wherein the M is Al(III).

56. The method of claim 49, which process is an enantioselective reaction.

57. The method of claim 49, which process is a diastereoselective reaction.

58. The method of claim 57, which diastereoselective reaction produces a kinetic resolution.

59. A method of resolving enantiomers from a racemic mixture of a chiral π-bond-containing substrate, or a racemic mixture of a chiral nucleophile having general formulas 1 and NuY, respectively:

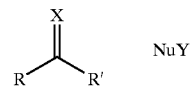

1 wherein

R, R', and R" represent, independently for each occurrence, hydrogen, alkyl, alkenyl, alkynyl, thioacyl, alkylthio, imine, phosphoryl, phosphonate, phosphine, carboxamide, anhydride, silyl, thioalkyl, alkylsulfonyl, arylsulfonyl, selenoalkyl, heteroalkyl, amidine, acetal, ketal, aryl, heteroaryl, aziridine, carbamate, epoxide, hydroxamic acid, imide, oxime, sulfonamide, thioamide, thiocarbamate, —C(O)$R_{10}$, —C(O)O$R_{10}$, —C(O)S$R_{10}$, —OC(O)$R_{10}$, —SC(O)$R_{10}$, —C(O)N($R_{11}$)$_2$, —N($R_{12}$)C(O)N($R_{12}$)$_2$, —N($R_{12}$)C(S)N($R_{12}$)$_2$, or —(CH$_2$)$_m$—$R_{80}$;

$R_{10}$ represents independently for each occurrence H, alkyl, alkenyl, or —(CH$_2$)$_m R_{80}$;

$R_{11}$ represents independently for each occurrence H, alkyl, alkenyl, —(CH$_2$)$_m$—$R_{80}$, —C(O)alkyl, —C(O)alkenyl, —C(O)alkynyl, or —C(O)(CH$_2$)$_m$—$R_{80}$; or two instances of $R_{11}$ are taken together with the N atom to which they are attached to form a heterocycle having from 4 to 8 atoms;

$R_{12}$ represents independently for each occurrence H, alkyl, or aralkyl;

X is selected from the group consisting of C(R)$_2$, O, S, Se and NR";

Y is selected, independently for each occurrence, from the group consisting of H, Li, Na, K, Mg, Ca, B, Al, Cu, Ag, Ti, Zr, Si(R)$_3$, and Sn(R)$_3$; and Nu is selected from the group consisting of conjugate bases of weak Bronsted acids and carbanions;

$R_{80}$ represents independently for each occurrence an unsubstituted or substituted aryl, a cycloalkyl, a cycloalkenyl, a heterocycle, or a polycycle; and m represents independently for each occurrence an integer in the range 0 to 8 inclusive;

the method comprising contacting said racemic mixture of the π-bond-containing substrate (1) or racemic mixture of the nucleophile with an achiral nucleophile or π-bond-containing substrate, respectively, able to react with the racemic substrate in the presence of a chiral catalyst having the form:

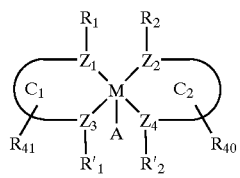

in which $Z_1$, $Z_2$, $Z_3$ and 4 each represent a Lewis base; the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents a main-group metal atom from Group 2, 12, 13, or 14;

A represents a counterion or a nucleophile; and wherein each $R_1$, $R_2$, $R'_1$, $R'_2$, $R_{40}$ and $R_{41}$ are selected to provide at least one stereogenic center in said tetradentate ligand, under conditions wherein one enantiomer of the racemic π-bond-containing substrate or racemic nucleophile reacts with an achiral nucleophile or π-bond-containing substrate, respectively, in a nucleophilic addition leaving the other enantiomer of the racemic substrate substantially unchanged.

60. The method of claim 59, wherein $R_1$, $R_2$, $R'_1$ and $R'_2$, occuring in 100 independently, represent hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—R$_7$;

each $R_{40}$ and $R_{41}$ occuring in 100 independently represent hydrogen, halogen, alkyl, alkenyl, alkynyl, hydroxyl, alkoxyl, silyloxy, amino, nitro, thiol, amine, imine, phosphoryl, phosphonate, phosphine, silyl, ether, thioether, sulfonyl, selenoether, —C(O)$R_{10}$, —C(O)O$R_{10}$, —C(O)S$R_{10}$, —OC(O)$R_{10}$, —SC(O)$R_{10}$, —C(O)N($R_{11}$)$_2$, or —(CH$_2$)$_m$—R$_7$;

$R_7$ represents independently for each occurrence aryl, cycloalkyl, cycloalkenyl, heterocycle, or polycycle;

$R_{10}$ represents independently for each occurrence H, alkyl, alkenyl, or —(CH$_2$)$_m$R$_7$;

$R_{11}$ represents independently for each occurrence H, alkyl, alkenyl, —(CH$_2$)$_m$—R$_{80}$, —C(O)alkyl, —C(O)alkenyl, —C(O)alkynyl, or —C(O)(CH$_2$)$_m$—R$_{80}$; or two instances of $R_{11}$ are taken together with the N atom to which they are attached to form a heterocycle having from 4 to 8 atoms; and m represents independently for each occurrence zero or an integer in the range of 1 to 8.

61. The method of claim 59, wherein each $Z_1$, $Z_2$, $Z_3$ and $Z_4$ are independently selected from the group consisting of nitrogen, oxygen, phosphorus, arsenic, and sulfur.

62. A method of providing a chiral, non-racemic α-amino nitrile, comprising reacting a prochiral or chiral imine with hydrogen cyanide, or a surrogate thereof, in the presence of a chiral, non-racemic catalyst such that a chiral, non-racemic α-amino nitrile is formed, wherein the chiral, non-racemic catalyst comprises an asymmetric tetradentate ligand complexed with a main-group metal atom from group 2, 12, 13, or 14; said complex having rectangular planar or rectangular pyramidal geometry, and said chiral, non-racemic catalyst is represented by general formula 100:

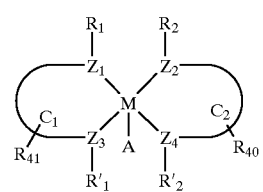

wherein $Z_1$, $Z_2$, $Z_3$ and $Z_4$ each represent a Lewis base;

the $C_1$ moiety, taken with $Z_1$, $Z_3$ and M, and the $C_2$ moiety taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached;

$R_{40}$ and $R_{41}$ each independently are absent, or represent one or more covalent substitutions of $C_1$ and $C_2$ with an organic or inorganic substituent permitted by valence requirements of the ring atom to which it is attached;

or any two or more of $R_1$, $R_2$, $R'_1$, $R'_2$, $R_{40}$ and $R_{41}$ taken together form a bridging substituent;

with the proviso that $C_1$ is substituted at at least one site by $R_1$, $R'_1$, or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as tetradentate;

M represents a main-group metal atom from Group 2, 12, 13, or 14;

A represents a counterion or a nucleophile; and each of $R_1$, $R_2$, $R'_1$, $R'_2$, $R_{40}$, and $R_{41}$ are selected to provide at least one stereogenic center in said tetradentate ligand.

63. The process of claim 1 or 14, wherein said Nu is cyanide, azide, isocyanate, thiocyanate, alkoxide, thioalkoxide, carboxylate, or thiocarboxylate.

64. The method of anyone of claims 25, 38, 49, or 59, wherein said Nu is cyanide, azide, isocyanate, thiocyanate, alkoxide, thioalkoxide, carboxylate, or thiocarboxylate.

* * * * *